(12) United States Patent
Liang

(10) Patent No.: US 8,198,276 B2
(45) Date of Patent: Jun. 12, 2012

(54) KINASE INHIBITOR COMPOUNDS

(75) Inventor: Congxin Liang, Palm Beach Gardens, FL (US)

(73) Assignee: Xcovery Holding Company LLC, West Palm Beach, FL (US)

( * ) Notice: Subject to any disclaimer, the term of this patent is extended or adjusted under 35 U.S.C. 154(b) by 305 days.

(21) Appl. No.: 12/451,833

(22) PCT Filed: Jun. 5, 2008

(86) PCT No.: PCT/US2008/007123
§ 371 (c)(1),
(2), (4) Date: Feb. 16, 2010

(87) PCT Pub. No.: WO2008/153942
PCT Pub. Date: Dec. 18, 2008

(65) Prior Publication Data
US 2010/0144768 A1     Jun. 10, 2010

Related U.S. Application Data

(60) Provisional application No. 60/933,385, filed on Jun. 6, 2007.

(51) Int. Cl.
*C07D 403/12*     (2006.01)
*A61K 31/505*     (2006.01)

(52) U.S. Cl. .................. 514/235.8; 514/269; 544/122; 544/319

(58) Field of Classification Search .......... 544/122, 544/319; 514/235.8, 252.14, 269
See application file for complete search history.

(56) References Cited

U.S. PATENT DOCUMENTS

2004/0242608 A1   12/2004   Durley
2007/0037808 A1    2/2007   Flynn et al.

FOREIGN PATENT DOCUMENTS
WO      2007/081901 A2     7/2007

OTHER PUBLICATIONS

Simone, Oncology: Introduction, Cecil Textbook of Medicine, 20th Edition, vol. 1, pp. 1004-1010, 1996.*
Bundgaard, Design of Prodrugs, p. 1, 1985.*
Wolff, Some consideration for prodrug design, Burger's Medicinal Chemistry and Drug Discovery, 5th Edition, vol. I: Principles and Practice, pp. 975-977, 1995.*
Banker et al., Prodrugs, Modern Pharmaceutics, Third Edition, Revised and Expanded, pp. 451 and 596.*
Damasio, Alzheimer's Disease and Related Dementias, Cecil Textbook of Medicine, $20^{th}$ Edition, vol. 2, pp. 1992-1996, 1996.*
Layzer, Degenerative Diseases of the Nervous System, Cecil Textbook of Medicine, $20^{th}$ Edition, vol. 2, pp. 2050-2057, 1996.*
West, Solid Solutions, Solid State Chemistry and its applications, pp. 358 & 365, 1988.*
Ulrich, Chapter 4: Crystal Characteristics, Kirk Othmer Encyclopedia of Chemical Technology (7 pages), Aug. 2002.*
Vippagunta et al., Crystalline Solids, Advanced Drug Delivery Reviews, 48, pp. 3-26, 2001.*
Douglas, Jr., "Introduction to Viral Diseases," Cecil Textbook of Medicine, 20th Edition, vol. 1 pp. 1739-1747 (1996).*
Gura, Systems for identifying New Drugs Are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
C. Dominguez et al., "p38 Inhibitors: Beyond Pyridinylimidazoles", Expert Opinion on Therapeutic Patents, 15(7), pp. 801-816 (2005).

* cited by examiner

*Primary Examiner* — Deepak Rao
(74) *Attorney, Agent, or Firm* — Jeffrey D. Hsi; Dwight D. Kim; Edwards Wildman Palmer LLP

(57) ABSTRACT

Pyrimidinone derivatives have enhanced and unexpected drug properties as inhibitors of protein kinases and are useful in treating disorders related to abnormal protein kinase activities such as inflammatory diseases and certain types of cancer.

6 Claims, No Drawings

KINASE INHIBITOR COMPOUNDS

CROSS-REFERENCE TO RELATED APPLICATIONS

This application is a 371 of PCT/US08/07123 filed Jun. 5, 2008 which claims priority benefit of U.S. Provisional application 60/933,385 file Jun. 6, 2007, the content of which is incorporated by reference in its entirety.

TECHNICAL FIELD OF THE INVENTION

This invention relates to novel pyrimidinone derivatives, their salts, solvates, hydrates and polymorphs thereof. The invention also provides compositions comprising a compound of this invention and the use of such compositions in methods of treating diseases and conditions associated with protein kinase modulation.

BACKGROUND OF THE INVENTION

Protein kinases are enzymes that catalyze the phosphorylation of hydroxyl groups of tyrosine, serine, and threonine residues of proteins. Many aspects of cell life (for example, cell growth, differentiation, proliferation, cell cycle and survival) depend on protein kinase activities. Furthermore, abnormal protein kinase activity has been related to a host of disorders such as cancer and inflammation. Therefore, considerable effort has been directed to identifying ways to modulate protein kinase activities. In particular, many attempts have been made to identify small molecules that act as protein kinase inhibitors.

Several pyrimidinone derivatives have demonstrated excellent activity as inhibitors of the p38 MAP kinases (see, e.g., WO2004/087677, WO2006/040649). The clinical utility of these compounds has been promising, but has been partially compromised due to the relatively poor aqueous solubility and/or other drug properties. What is needed is a class of modified pyrimidinone derivatives having both inhibitory activity and enhanced potency and/or drug properties.

The p38 MAP kinase is activated by a variety of signals including proinflammatory cytokines such as tumor necrosis factor (TNF) and interleukin-1 (IL-1), as well as bacterial lipopolysaccharides and environmental stress such as osmotic shock and ultraviolet radiation (Ono, K. and J. Han, Cell Signal. 12: 1, 2000). Within the p38 kinase family, there are four distinct isozymes: p38 alpha, p38 beta, p38 gamma, and p38 delta. The p38 kinase family function downstream of an activating stimulus by phosphorylating and activating transcription factors (e.g. ATF2, CHOP and MEF2C) as well as other kinases (e.g. MAPKAP-2 and MAPKAP-3) (Trends in Cell biology 7, 353-361, 1997; Mol Cell Biology 19, 21-30, 1999; EMBO J 20, 466-479, 2001). Upon activation, the p38 kinase cascade leads to the induction of gene expression of several factors involved in inflammation and immunity including TNF, interleukin-6, granulocyte-macrophage colony stimulating factor (GM-CSF), and HIV long terminal repeat (Paul et al., Cell Signal. 9: 403-410, 1997). The products of the p38 phosphorylation stimulate the production of inflammatory cytokines and other proteins, including TNF and IL-1, and cyclooxygenase-2, and also possibly modulate the effects of these cytokines on their target cells, and thus stimulate inflammation processes (Lee, J. C. et al, Nature, 372: 376, 1994).

P38 MAP kinases have also been shown to promote apoptosis during ischemia in cardiac myocytes, which suggests that p38 MAP kinase inhibitors can be used to treat ischemic heart disease (J. Biol. Chem. 274, 6272, 1999). They are also required for T-cell HIV-1 replication and may be useful targets for AIDS therapy. P38 pathway inhibitors have been used to increase cancer cell sensitivity to cancer therapy, have also find use in the treatment of asthma (JPET 293, 281, 2000).

TNF is a cytokine and a potent proinflammatory mediator implicated in inflammatory conditions such as arthritis, asthma, septic shock, non-insulin dependent diabetes mellitus, multiple sclerosis, asthma, and inflammatory bowel disease. Thus inhibitors of p38 MAP kinases (required for TNF production) may be useful for the treatment of inflammatory conditions resulting from excessive cytokine production such as arthritis. (Boehm, J. C. and J. L. Adams, Exp. Opin. Ther. Patents 10: 25, 2000, and references cited therein). TNF has also been implicated in viral infections, such as HIV, influenza virus, and herpes virus including herpes simplex virus type-1 (HSV-1), herpes simplex virus type-2 (HSV-2), cytomegalovirus (CMV), varicella-zoster virus (VZV), Epstein-Barr virus, human herpesvirus-6 (HHV-6), human herpesvirus-7(HHV-7), human herpesvirus-8 (HHV-8), pseudorabies and rhinotracheitis, among others.

Excessive or unregulated TNF production has also been shown to produce elevated levels of IL-1. Inhibition of TNF, therefore, should reduce levels of IL-1 (European Cytokine Netw 6, 225, 1995) and ameliorate disease states caused by unregulated IL-1 synthesis. Such disease states include rheumatoid arthritis, rheumatoid spondylitis, osteoarthritis, gouty arthritis, sepsis, septic shock, endotoxic shock, gram negative sepsis, toxic shock syndrome, adult respiratory distress syndrome, cerebral malaria, chronic pulmonary inflammatory disease, silicosis, pulmonary sarcosis, bone resorption diseases, reperfusion injury, graft versus host reaction, alallograft rejections, fever and myalgias due to infection, cachexia secondary to infection or malignancy, cachexia secondary to acquired immune deficiency syndrome (AIDS), AIDS related complex (ARC), keloid formation, scar tissue formation, Crohn's disease, ulcerative colitis, and pyresis.

IL-1 has also been shown to mediate a variety of biological activities such as the activation of T-helper cells, induction of fever, stimulation of prostaglandin or collagenase production, neutrophil chemotaxis, and the suppression of plasma iron levels (Rev. Infect. Disease, 6, 51,(1984)). Elevated levels of IL-1 have also been implicated in mediating or exacerbating a number of disease states including rheumatoid arthritis, osteoarthritis, rheumatoid spondylitis, gouty arthritis, inflammatory bowel disease, adult respiratory distress syndrome (ARDS), psoriasis, Crohn's disease, ulcerative colitis, anaphylaxis, muscle degeneration, cachexia, Reiter's syndrome, type I and type I1 diabetes, bone resorption diseases, ischemia reperfusion injury, arteriosclerosis, brain trauma, multiple sclerosis, sepsis, septic shock, and toxic shock syndrome. Viruses sensitive to TNF inhibition, such as HIV-1, HIV-2, HIV-3, are also affected by IL-1 production. In rheumatoid arthritis, both IL-1 and TNF induce collagenase synthesis and ultimately lead to tissue destruction within arthritic joints (Lymphokine Cytokine Res.(11), 253-256, (1992) and Clin. Exp. Immunol. 989, 244-250,(1992)).

IL-6 is another pro-inflammatory cytokine, which is associated with many conditions including inflammation. Consequently, TNF, IL-1 and IL-6 affect a wide variety of cells and tissues and are important inflammatory mediators of a wide variety of disease states and conditions. The inhibition of these cytokines by inhibition or modulation of p38 kinase is of benefit in controlling, reducing and alleviating many of these disease states and conditions. Therefore, the invention concerns finding small molecule inhibitors or modulators of p38 kinase and the p38 kinase pathway.

It is therefore desirable to create new and alternative approaches to addressing treatment and prevention of disease, disorders, or symptoms thereof.

SUMMARY OF THE INVENTION

The invention relates to pyrimidinone derivative compounds, compositions comprising the compounds, and methods of using the compounds and compound compositions. The compounds and compositions comprising them are useful for treating or preventing disease or disease symptoms, including those mediated by or associated with protein kinase modulation activity.

The present invention solves the problems set forth above by providing an isolated compound of Formula I:

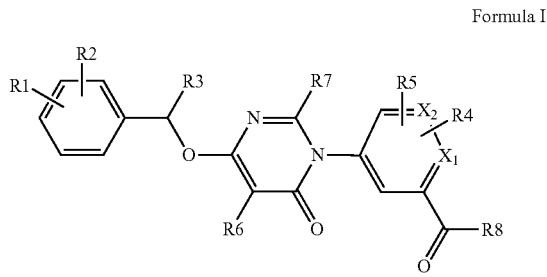

Formula I or a salt thereof; or a prodrug, or a salt of a prodrug thereof; or a hydrate, solvate, or polymorph thereof; wherein:

$R^1$, $R^2$, $R^3$, $R^4$, $R^5$, $R^6$ are each independently hydrogen, halo, (C1-C3) alkyl, (C1-C3) alkoxy, or (C1-C3) alkylamino;

$R^7$ is hydrogen, halo, (C1-C6) alkyl, (C1-C6) alkoxy, and (C1-C6) alkylamino wherein the alkyl is optionally substituted by one or two groups that are independently hydroxyl, (C1-C3) alkoxy, and (C1-C3) alkylamino;

$R^8$ is C(O)NR$^9$R$^{10}$ or NHR$^{11}$;

$R^9$ and $R^{10}$ are each independently hydrogen, (C1-C6) alkyl, (C3-C8) cycloalkyl, (C3-C8) heterocyclyl, or $R^9$ and $R^{10}$ together with the nitrogen they are attached to form a (C3-C8) heterocycle;

$R^{11}$ is a (C3-C8) cycloalkyl or (C3-C8) heterocycle provided that the cycloalkyl or heterocycle is substituted by 1, 2, 3, or 4 groups that are independently oxo, hydroxyl, (C1-C6) alkyl, (C1-C3) alkoxy, (C1-C3) alkylamino, heterocycle, amide, hydroxyl(C1-C6)alkyl, or (C1-C3)alkoxy(C1-C3) alkyl;

$X^1$, $X^2$ are each independently N or CR$^4$.

The compounds of this invention, and compositions comprising them, are useful for treating or lessening the severity of protein kinase modulated diseases, disorders, or symptoms thereof, i.e., disorders effectively treated by inhibitors of protein kinases, e.g., p38α.

In another aspect, the invention relates to a method of treating a disease or disease symptom in a subject in need thereof including administering to the subject an effective amount of a compound of any of the formulae herein, or pharmaceutical salt, solvate or hydrate thereof (or composition thereof). The disease or disease symptom can be any of those modulated by a protein kinase (e.g., p38α). The disease or disease symptom can be, for example, an inflammatory disease or disorder, or a cancer or proliferation disease or disorder.

DETAILED DESCRIPTION OF THE INVENTION

Definitions

The terms "ameliorate" and "treat" are used interchangeably and both mean decrease, suppress, attenuate, diminish, arrest, or stabilize the development or progression of a disease (e.g., a disease or disorder delineated herein).

By "disease" is meant any condition or disorder that damages or interferes with the normal function of a cell, tissue, or organ.

By "marker" is meant any alteration that is associated with a disease or disorder. For example, any protein or polynucleotide having an alteration in expression level or activity that is associated with a disease or disorder.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

The term "compound" as used herein, is also intended to include salts, prodrugs, and prodrug salts of a compound of formulae herein. The term also includes any solvates, hydrates, and polymorphs of any of the foregoing. The specific recitation of "prodrug," "prodrug salt," "solvate," "hydrate," or "polymorph" in certain aspects of the invention described in this application shall not be interpreted as an intended omission of these forms in other aspects of the invention where the term "compound" is used without recitation of these other forms.

A salt of a compound of this invention is formed between an acid and a basic group of the compound, such as an amino functional group, or a base and an acidic group of the compound, such as a carboxyl functional group. According to another preferred embodiment, the compound is a pharmaceutically acceptable acid addition salt.

As used herein and unless otherwise indicated, the term "prodrug" means a derivative of a compound that can hydrolyze, oxidize, or otherwise react under biological conditions (in vitro or in vivo) to provide a compound of this invention. Prodrugs may only become active upon such reaction under biological conditions, or they may have activity in their unreacted forms. Examples of prodrugs contemplated in this invention include, but are not limited to, analogs or derivatives of compounds of any one of the formulae disclosed herein that comprise biohydrolyzable moieties such as amides, esters, carbamates, carbonates, and phosphate analogues. Prodrugs can typically be prepared using well-known methods, such as those described by Burger's Medicinal Chemistry and Drug Discovery (1995) 172-178, 949-982 (Manfred E. Wolff ed., 5th ed); see also Goodman and Gilman's, The Pharmacological basis of Therapeutics, 8th ed., McGraw-Hill, Int. Ed. 1992, "Biotransformation of Drugs".

As used herein and unless otherwise indicated, the term "biohydrolyzable moiety" means a functional group (e.g., amide, ester, carbamate, carbonate, or phosphate analogue, that either: 1) does not destroy the biological activity of the compound and confers upon that compound advantageous properties in vivo, such as uptake, duration of action, or onset of action; or 2) is itself biologically inactive but is converted in vivo to a biologically active compound.

A prodrug salt is a compound formed between an acid and a basic group of the prodrug, such as an amino functional group, or a base and an acidic group of the prodrug, such as a carboxyl functional group. In a one embodiment, the prodrug salt is a pharmaceutically acceptable salt.

Particularly favored prodrugs and prodrug salts are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or central nervous system) relative to the parent species. Preferred prodrugs include derivatives where a group that enhances aqueous solubility or active transport through the gut membrane is appended to the structure of formulae described herein. See, e.g., Alexander, J. et al. Journal of Medicinal Chemistry 1988, 31, 318-322; Bundgaard, H. Design of Prodrugs; Elsevier: Amsterdam, 1985; pp 1-92; Bundgaard, H.; Nielsen, N. M. Journal of Medicinal Chemistry 1987, 30, 451-454; Bundgaard, H. A Textbook of Drug Design and Development; Harwood Academic Publ.: Switzerland, 1991; pp 113-191; Digenis, G. A. et al. Handbook of Experimental Pharmacology 1975, 28, 86-112; Friis, G. J.; Bundgaard, H. A Textbook of Drug Design and Development; 2 ed.; Overseas Publ.: Amsterdam, 1996; pp 351-385; Pitman, I. H. Medicinal Research Reviews 1981, 1, 189-214.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound or a prodrug of a compound of this invention.

Acids commonly employed to form pharmaceutically acceptable salts include inorganic acids such as hydrogen bisulfide, hydrochloric, hydrobromic, hydroiodic, sulfuric and phosphoric acid, as well as organic acids such as para-toluenesulfonic, salicylic, tartaric, bitartaric, ascorbic, maleic, besylic, fumaric, gluconic, glucuronic, formic, glutamic, methanesulfonic, ethanesulfonic, benzenesulfonic, lactic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and the like salts. Preferred pharmaceutically acceptable acid addition salts include those formed with mineral acids such as hydrochloric acid and hydrobromic acid, and especially those formed with organic acids such as maleic acid.

Suitable bases for forming pharmaceutically acceptable salts with acidic functional groups of prodrugs of this invention include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like.

As used herein, the term "hydrate" means a compound which further includes a stoichiometric or non-stoichiometric amount of water bound by non-covalent intermolecular forces.

As used herein, the term "solvate" means a compound which further includes a stoichiometric or non-stoichiometric amount of solvent such as water, acetone, ethanol, methanol, dichloromethane, 2-propanol, or the like, bound by non-covalent intermolecular forces.

As used herein, the term "polymorph" means solid crystalline forms of a compound or complex thereof which may be characterized by physical means such as, for instance, X-ray powder diffraction patterns or infrared spectroscopy. Different polymorphs of the same compound can exhibit different physical, chemical and/or spectroscopic properties. Different physical properties include, but are not limited to stability (e.g., to heat, light or moisture), compressibility and density (important in formulation and product manufacturing), hygroscopicity, solubility, and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

The term "substantially free of other stereoisomers" as used herein means less than 25% of other stereoisomers, preferably less than 10% of other stereoisomers, more preferably less than 5% of other stereoisomers and most preferably less than 2% of other stereoisomers, or less than "X"% of other stereoisomers (wherein X is a number between 0 and 100, inclusive) are present. Methods of obtaining or synthesizing diastereomers are well known in the art and may be applied as practicable to final compounds or to starting material or intermediates. Other embodiments are those wherein the compound is an isolated compound. The term "at least X % enantiomerically enriched" as used herein means that at least X % of the compound is a single enantiomeric form, wherein X is a number between 0 and 100, inclusive.

The term "stable compounds", as used herein, refers to compounds which possess stability sufficient to allow manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"Stereoisomer" refers to both enantiomers and diastereomers.

As used herein, the term "halo" or "halogen" refers to any radical of fluorine, chlorine, bromine or iodine.

The terms "alk" or "alkyl" refer to straight or branched chain hydrocarbon groups having 1 to 12 carbon atoms, preferably 1 to 8 carbon atoms. The expression "lower alkyl" refers to alkyl groups of 1 to 4 carbon atoms (inclusive). The term "arylalkyl" refers to a moiety in which an alkyl hydrogen atom is replaced by an aryl group. The term "alkenyl" refers to straight or branched chain hydrocarbon groups of 2 to 10, preferably 2 to 4, carbon atoms having at least one double bond. Where an alkenyl group is bonded to a nitrogen atom, it is preferred that such group not be bonded directly through a carbon bearing a double bond.

The term "alkoxy" refers to an —O-alkyl radical. The term "alkylenedioxo" refers to a divalent species of the structure —O—R—O, in which R represents an alkylene.

The term "alkynyl" refers to straight or branched chain hydrocarbon groups of 2 to 10, preferably 2 to 4, carbon atoms having at least one triple bond. Where an alkynyl group is bonded to a nitrogen atom, it is preferred that such group not be bonded directly through a carbon bearing a triple bond.

The term "alkylene" refers to a divalent straight chain bridge of 1 to 5 carbon atoms connected by single bonds (e.g., —(CH$_2$)$_x$—, wherein x is 1 to 5), which may be substituted with 1 to 3 lower alkyl groups.

The term "alkenylene" refers to a straight chain bridge of 2 to 5 carbon atoms having one or two double bonds that is connected by single bonds and may be substituted with 1 to 3 lower alkyl groups. Exemplary alkenylene groups are —CH=CH—CH=CH—, —CH$_2$—CH=CH—, —CH$_2$—CH=CH—CH$_2$—, —C(CH$_3$)$_2$CH=CH— and —CH(C$_2$H$_5$)—CH=CH—.

The term "alkynylene" refers to a straight chain bridge of 2 to 5 carbon atoms that has a triple bond therein, is connected by single bonds, and may be substituted with 1 to 3 lower alkyl groups. Exemplary alkynylene groups are —CC—, —CH$_2$—CC—, —CH(CH$_3$)—CC— and —CC—CH(C$_2$H$_5$)CH$_2$—.

The terms "cycloalkyl" and "cycloalkenyl" as employed herein includes saturated and partially unsaturated cyclic, respectively, hydrocarbon groups having 3 to 12 carbons, preferably 3 to 8 carbons, and more preferably 3 to 6 carbon.

The terms "Ar" or "aryl" refer to aromatic cyclic groups (for example 6 membered monocyclic, 10 membered bicyclic or 14 membered tricyclic ring systems) which contain 6 to 14 carbon atoms. Exemplary aryl groups include phenyl, naphthyl, biphenyl and anthracene.

Heteroaryl" refers to a monocyclic or fused ring (i.e., rings which share an adjacent pair of atoms) group of 5 to 12 ring atoms containing one, two, three or four ring heteroatoms selected from N, O, or S, the remaining ring atoms being C, and, in addition, having a completely conjugated pi-electron system, wherein 0, 1, 2, 3, or 4 atoms of each ring may be substituted by a substituent. Examples, without limitation, of heteroaryl groups are pyrrole, furan, thiophene, imidazole, oxazole, thiazole, pyrazole, pyridine, pyrimidine, quinoline, quinazoline, isoquinoline, purine and carbazole.

The terms "heterocycle", "heterocyclic" or "heterocyclo" refer to fully saturated or partially unsaturated cyclic groups, for example, 3 to 7 membered monocyclic, 7 to 12 membered bicyclic, or 10 to 15 membered tricyclic ring systems, which have at least one heteroatom in at least one ring, wherein 0, 1, 2 or 3 atoms of each ring may be substituted by a substituent. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system.

The term "substituents" refers to a group "substituted" on any functional group delineated herein, e.g., alkyl, alkenyl, alkynyl, cycloalkyl, cycloalkenyl, aryl, heterocyclyl, or heteroaryl group at any atom of that group. Suitable substituents include, without limitation halogen, CN, NO$_2$, OR$^{15}$, SR$^{15}$, S(O)$_2$OR$^{15}$, NR$^{15}$R$^{16}$, C$_1$-C$_2$perfluoroalkyl, C$_1$-C$_2$ perfluoroalkoxy, 1,2-methylenedioxy, C(O)OR$^{15}$, C(O)NR$^{15}$R$^{16}$, OC(O)NR$^{15}$R$^{16}$, NR$^{15}$C(O)NR$^{15}$R$^{16}$, C(NR$^{16}$)NR$^{15}$R$^{16}$, NR$^{15}$C(NR$^{16}$)NR$^{15}$R$^{16}$, S(O)$_2$NR$^{15}$R$^{16}$,R$^{17}$, C(O)R$^{17}$, NR$^{15}$C(O)R$^{17}$, S(O)R$^{17}$, S(O)$_2$R$^{17}$, R$^{16}$, oxo, C(O)R$^{16}$, C(O)(CH$_2$)nOH, (CH$_2$)nOR$^{15}$, (CH$_2$)nC(O)NR$^{15}$,R$^{16}$, NR$^{15}$S(O)$_2$R$^{17}$, where n is independently 0-6 inclusive. Each R$^{15}$ is independently hydrogen, C$_1$-C$_4$ alkyl or C$_3$-C$_6$ cycloalkyl. Each R$^{16}$ is independently hydrogen, C$_3$-C$_6$ cycloalkyl, aryl, heterocyclyl, heteroaryl, C$_1$-C$_4$ alkyl or C$_1$-C$_4$ alkyl substituted with C$_3$-C$_6$ cycloalkyl, aryl, heterocyclyl or heteroaryl. Each R$^{17}$ is independently C$_3$-C$_6$ cycloalkyl, aryl, heterocyclyl, heteroaryl, C$_1$-C$_4$ alkyl or C$_1$-C$_4$ alkyl substituted with C$_3$-C$_6$ cycloalkyl, aryl, heterocyclyl or heteroaryl. Each C$_3$-C$_6$ cycloalkyl, aryl, heterocyclyl, heteroaryl and C$_1$-C$_4$ alkyl in each R$^{15}$, R$^{16}$ and R$^{17}$ can optionally be substituted with halogen, CN, C$_1$-C$_4$ alkyl, OH, C$_1$-C$_4$ alkoxy, NH$_2$, C$_1$-C$_4$ alkylamino, C$_1$-C$_4$ dialkylamino, C$_1$-C$_2$perfluoroalkyl, C$_1$-C$_2$ perfluoroalkoxy, or 1,2-methylenedioxy.

The term "oxo" refers to an oxygen atom, which forms a carbonyl when attached to carbon, an N-oxide when attached to nitrogen, and a sulfoxide or sulfone when attached to sulfur.

The term "acyl" refers to an alkylcarbonyl, cycloalkylcarbonyl, arylcarbonyl, heterocyclylcarbonyl, or heteroarylcarbonyl substituent, any of which may be further substituted by substituents.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

The compounds of this invention may contain one or more asymmetric centers and thus occur as racemates and racemic mixtures, single enantiomers, individual diastereomers and diastereomeric mixtures. All such isomeric forms of these compounds are expressly included in the present invention. The compounds of this invention may also be represented in multiple tautomeric forms, in such instances, the invention expressly includes all tautomeric forms of the compounds described herein. All such isomeric forms of such compounds are expressly included in the present invention. All crystal forms of the compounds described herein are expressly included in the present invention.

The present invention provides a compound of Formula I:

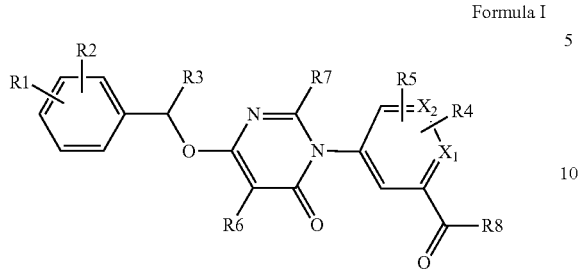

Formula I or a salt thereof; or a prodrug, or a salt of a prodrug thereof; or a hydrate, solvate, or polymorph thereof; wherein:

$R^1$, $R^2$, $R^3$, $R^4$, $R^5$, $R^6$ are each independently hydrogen, halo, (C1-C3) alkyl, (C1-C3) alkoxy, and (C1-C3) alkylamino;

$R^7$ is hydrogen, halo, (C1-C6) alkyl, (C1-C6) alkoxy, and (C1-C6) alkylamino wherein the alkyl is optionally substituted by one or two groups that are independently hydroxyl, (C1-C3) alkoxy, and (C1-C3) alkylamino;

$R^8$ is $C(O)NR^9R^{10}$ or $NHR^{11}$;

$R^9$ and $R^{10}$ are each independently hydrogen, (C1-C6) alkyl, (C3-C8) cycloalkyl, (C3-C8) heterocyclyl, or $R^9$ and $R^{10}$ together with the nitrogen they are attached to form a (C3-C8) heterocycle;

$R^{11}$ is a (C3-C8) cycloalkyl or (C3-C8) heterocycle provided that the cycloalkyl or heterocycle is substituted by 1, 2, 3, or 4 groups that are independently oxo, hydroxyl, (C1-C6) alkyl, (C1-C3) alkoxy, (C1-C3) alkylamino, heterocycle, amide, hydroxyl(C1-C6)alkyl, or (C1-C3)alkoxy(C1-C3)alkyl;

$X^1$, $X^2$ are each independently N or $CR^4$.

In one aspect, the compounds are of any of the formulae herein, wherein $R^8$ is $C(O)NR^9R^{10}$ and $R^9$ and $R^{10}$ are each independently hydrogen, (C1-C6) alkyl, (C3-C8) cycloalkyl, (C3-C8) heterocyclyl, or $R^9$ and $R^{10}$ together with the nitrogen they are attached to form a (C3-C8) heterocycle.

In one aspect, the compounds are of any of the formulae herein, wherein $R^{11}$ is a 3-8 membered cycloalkyl substituted by 1, 2, 3, or 4 groups that are independently oxo, hydroxyl, (C1-C6)alkyl, (C1-C3) alkoxy, (C1-C3) alkylamino, heterocycle, amide, hydroxyl(C1-C6)alkyl, or (C1-C3)alkoxy(C1-C3)alkyl.

In one aspect, the compounds are of any of the formulae herein, wherein $R^{11}$ is a 3-8 membered heterocycle substituted by 1, 2, 3, or 4 groups that are independently oxo, hydroxyl, (C1-C6)alkyl, (C1-C3) alkoxy, (C1-C3) alkylamino, heterocycle, amide, hydroxyl(C1-C6)alkyl, or (C1-C3)alkoxy(C1-C3)alkyl.

In one aspect, the compounds are of any of the formulae herein, wherein $X^1$, $X^2$ are each independently $CR^4$.

In one aspect, the compound is a compound of Table 1.

Representative compounds of the invention are depicted in Table 1. In these examples the stereochemistry at the chiral carbon atoms is independently either RS, R, or S. The Table 1 structures contain certain —NH— (amino) and —OH (hydroxyl) groups where the corresponding hydrogen atom does not explicitly appear; however they are to be read as —NH— or —OH as the case may be.

TABLE 1

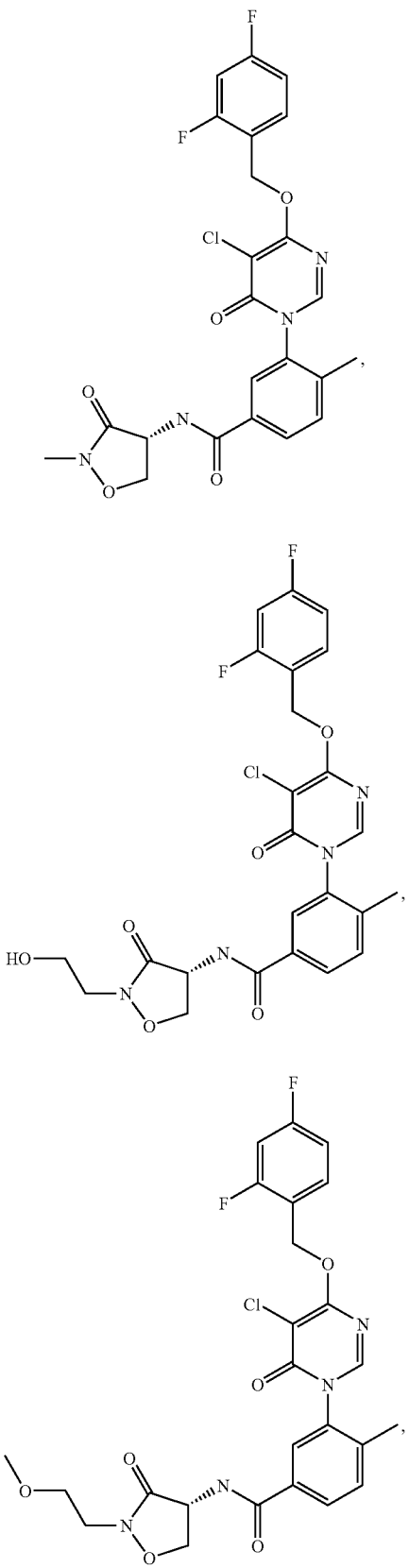

TABLE 1-continued
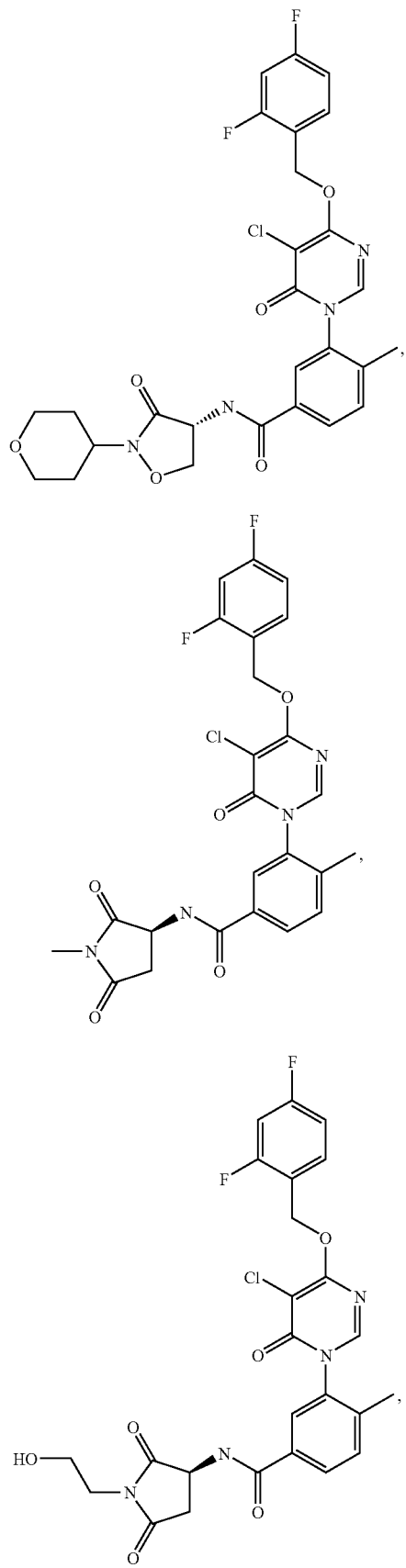
TABLE 1-continued
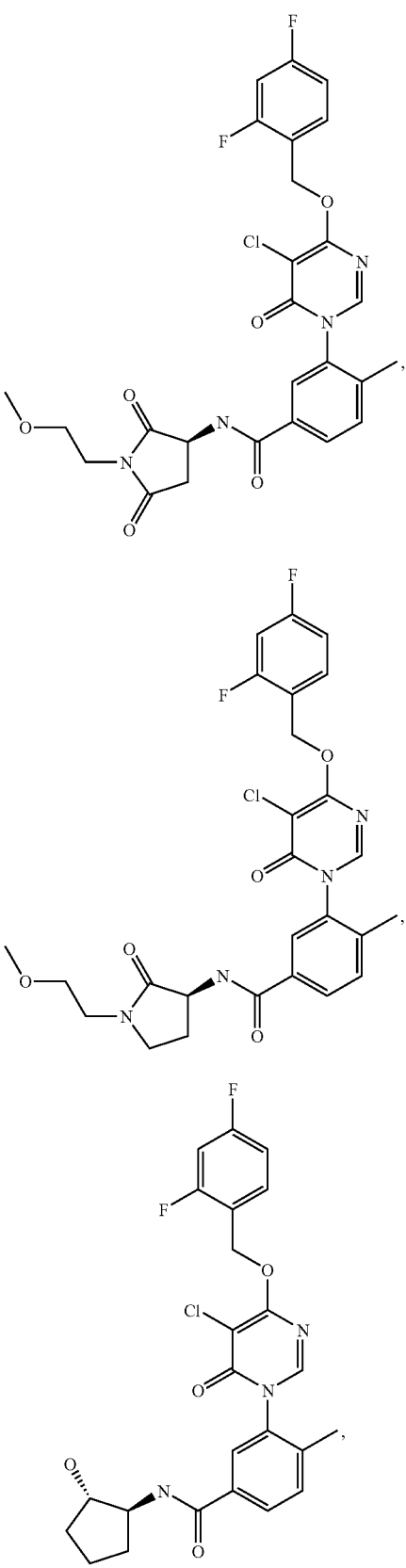

TABLE 1-continued

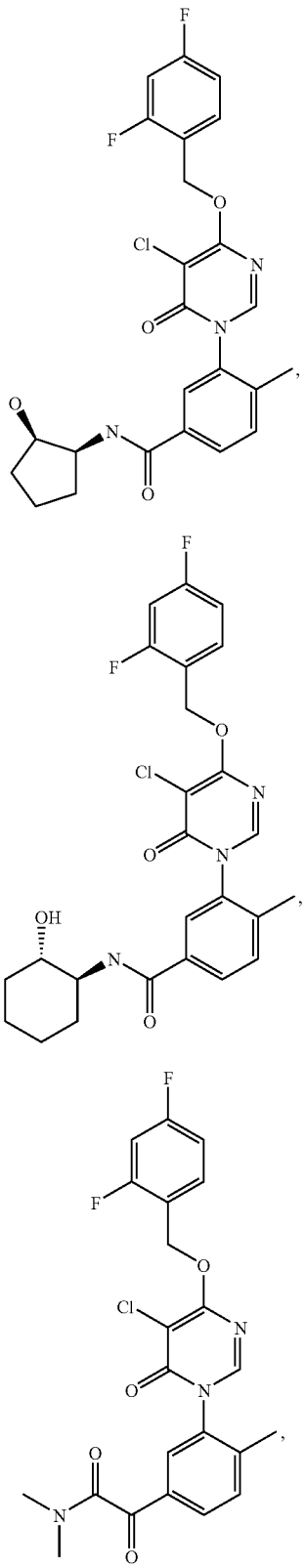

TABLE 1-continued

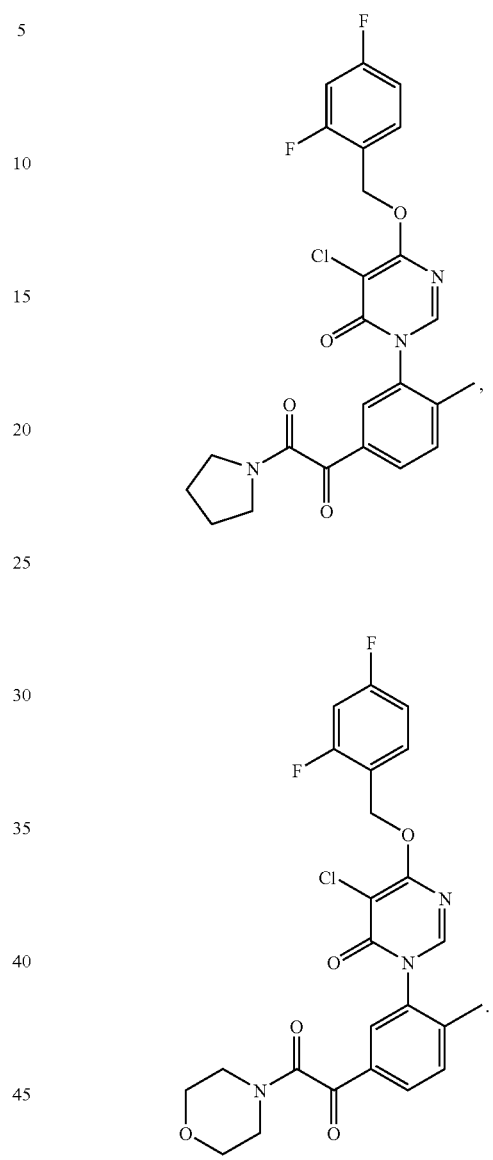

The synthesis of compounds of the formulae herein (e.g., Formula I) can be readily effected by synthetic chemists of ordinary skill. Relevant procedures and intermediates are disclosed, for instance, herein. Each of the patents, patent applications, and publications, whether in traditional journals or available only through the internet, referred to herein, is incorporated in its entirety by reference.

A convenient method for producing compounds of the formulae herein (e.g., Formula I) involves the synthesis of the common intermediate, 3-[5-Chloro-4-(2,4-difluoro-benzyloxy)-6-oxo-6H-pyrimidin-1-yl]-4-methyl-benzoic acid, followed by derivatization using different amines as shown below:

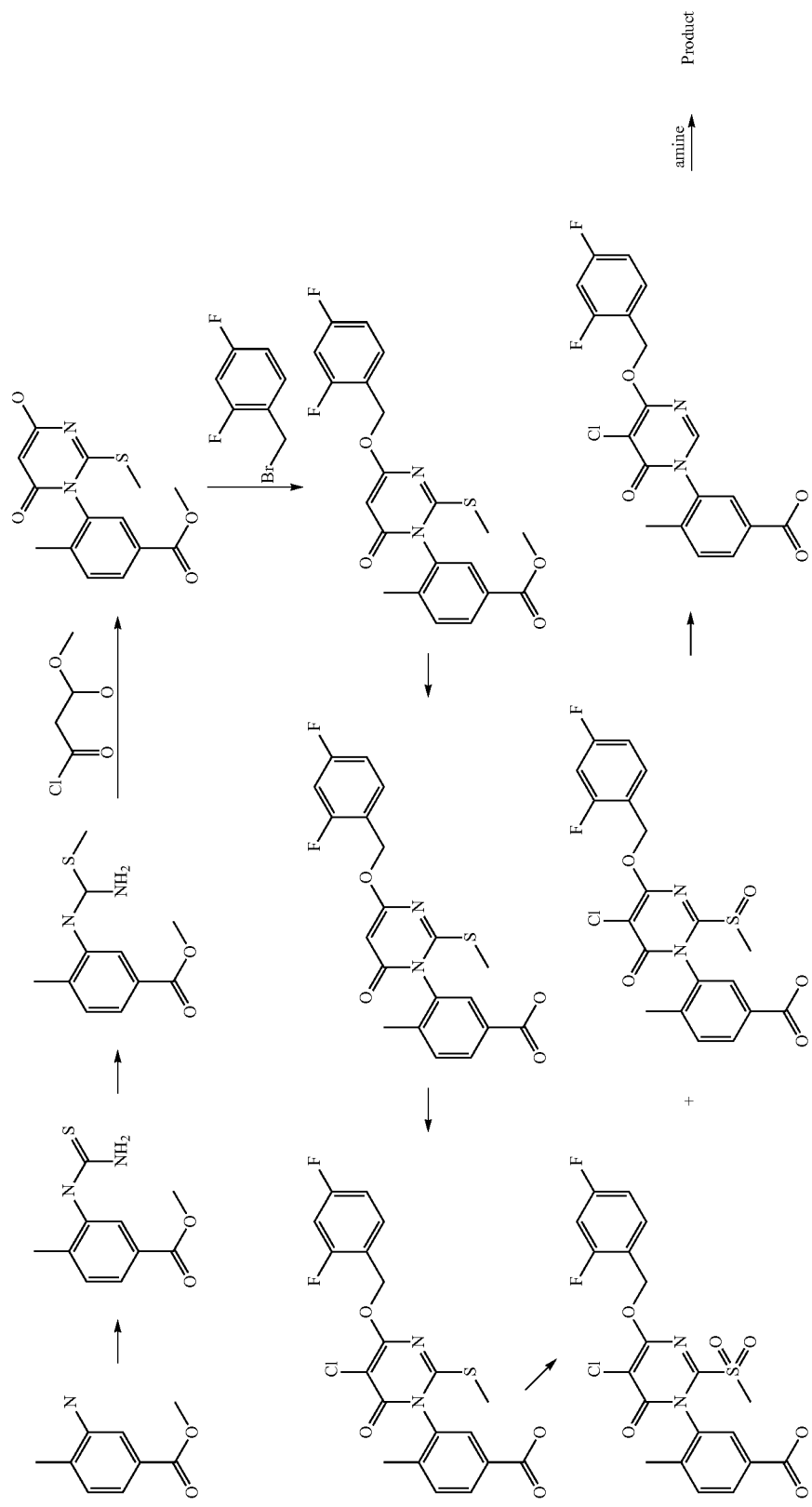

Other approaches to synthesizing compounds of the formulae herein (e.g., Formula I) can readily be adapted from references cited herein. Variations of these procedures and their optimization are within the skill of the ordinary practitioner.

The specific approaches and compounds shown above are not intended to be limiting. The chemical structures in the schemes herein depict variables that are hereby defined commensurately with chemical group definitions (moieties, atoms, etc.) of the corresponding position in the compound formulae herein, whether identified by the same variable name (e.g., $R^1$, $R^2$, R, R', X, etc.) or not. The suitability of a chemical group in a compound structure for use in synthesis of another compound structure is within the knowledge of one of ordinary skill in the art. Additional methods of synthesizing compounds of the formulae herein (e.g., Formula I) and their synthetic precursors, including those within routes not explicitly shown in schemes herein, are within the means of chemists of ordinary skill in the art. Methods for optimizing reaction conditions, if necessary minimizing competing by-products, are known in the art. The methods described herein may also additionally include steps, either before or after the steps described specifically herein, to add or remove suitable protecting groups in order to ultimately allow synthesis of the compounds herein. In addition, various synthetic steps may be performed in an alternate sequence or order to give the desired compounds. Synthetic chemistry transformations and protecting group methodologies (protection and deprotection) useful in synthesizing the applicable compounds are known in the art and include, for example, those described in R. Larock, *Comprehensive Organic Transformations*, VCH Publishers (1989); T. W. Greene and P. G. M. Wuts, *Protective Groups in Organic Synthesis*, $3^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The synthetic methods described herein may also additionally include steps, either before or after any of the steps described in any scheme, to add or remove suitable protecting groups in order to ultimately allow synthesis of the compound of the formulae described herein. The methods delineated herein contemplate converting compounds of one formula to compounds of another formula. The process of converting refers to one or more chemical transformations, which can be performed in situ, or with isolation of intermediate compounds. The transformations can include reacting the starting compounds or intermediates with additional reagents using techniques and protocols known in the art, including those in the references cited herein. Intermediates can be used with or without purification (e.g., filtration, distillation, sublimation, crystallization, trituration, solid phase extraction, and chromatography).

Combinations of substituents and variables envisioned by this invention are only those that result in the formation of stable compounds.

The invention also provides compositions comprising an effective amount of a compound of any of the formulae herein (e.g., Formula I), or a pharmaceutically acceptable salt, solvate, hydrate, polymorph or prodrug, if applicable, of said compound; and an acceptable carrier. Preferably, a composition of this invention is formulated for pharmaceutical use ("a pharmaceutical composition"), wherein the carrier is a pharmaceutically acceptable carrier. The carrier(s) must be "acceptable" in the sense of being compatible with the other ingredients of the formulation and, in the case of a pharmaceutically acceptable carrier, not deleterious to the recipient thereof in amounts typically used in medicaments.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch). Other formulations may conveniently be presented in unit dosage form, e.g., tablets and sustained release capsules, and in liposomes, and may be prepared by any methods well known in the art of pharmacy. See, for example, Remington's Pharmaceutical Sciences, Mack Publishing Company, Philadelphia, Pa. (17th ed. 1985).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers or both, and then if necessary shaping the product.

In certain preferred embodiments, the compound is administered orally. Compositions of the present invention suitable for oral administration may be presented as discrete units such as capsules, sachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion, or packed in liposomes and as a bolus, etc. Soft gelatin capsules can be useful for containing such suspensions, which may beneficially increase the rate of compound absorption.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface-active or dispersing agent. Molded tablets may be made by molding in a suitable machine a mixture of the powdered compound moistened with an inert liquid diluent. The tablets optionally may be coated or scored and may be formulated so as to provide slow or controlled release of the active ingredient therein. Methods of formulating such slow or controlled release compositions of pharmaceutically active ingredients, such as those herein and other compounds known in the art, are known in the art and described in several issued US Patents, some of which include, but are not limited to, U.S. Pat. Nos. 4,369,172; and 4,842,866, and references cited therein. Coatings can be used for delivery of compounds to the intestine (see, e.g., U.S. Pat. Nos. 6,638,534, 5,217,720, and 6,569,457, 6,461,631, 6,528, 080, 6,800,663, and references cited therein). A useful formulation for the compounds of this invention is the form of enteric pellets of which the enteric layer comprises hydroxypropylmethylcellulose acetate succinate.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for topical administration include lozenges comprising the ingredients in a flavored basis, usually sucrose and acacia or tragacanth; and pastilles comprising the active ingredient in an inert basis such, as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches and iontophoretic administration are also included in this invention.

Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or central nervous system) relative to the parent species. Preferred prodrugs include derivatives where a group that enhances aqueous solubility or active transport through the gut membrane is appended to the structure of formulae described herein. See, e.g., Alexander, J. et al. *Journal of Medicinal Chemistry* 1988, 31, 318-322; Bundgaard, H. *Design of Prodrugs*; Elsevier: Amsterdam, 1985; pp 1-92; Bundgaard, H.; Nielsen, N. M. *Journal of Medicinal Chemistry* 1987, 30, 451-454; Bundgaard, H. *A Textbook of Drug Design and Development*; Harwood Academic Publ.: Switzerland, 1991; pp 113-191; Digenis, G. A. et al. *Handbook of Experimental Pharmacology* 1975, 28, 86-112; Friis, G. J.; Bundgaard, H. *A Textbook of Drug Design and Development;* 2 ed.; Overseas Publ.: Amsterdam, 1996; pp 351-385; Pitman, I. H. *Medicinal Research Reviews* 1981, 1, 189-214.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

According to another embodiment, the invention provides a method of impregnating an implantable drug release device comprising the step of contacting said drug release device with a compound or composition of this invention. Implantable drug release devices include, but are not limited to, biodegradable polymer capsules or bullets, non-degradable, diffusible polymer capsules and biodegradable polymer wafers.

According to another embodiment, the invention provides an implantable medical device coated with a compound or a composition comprising a compound of this invention, such that said compound is therapeutically active.

In another embodiment, a composition of the present invention further comprises a second therapeutic agent. The second therapeutic agent includes any compound or therapeutic agent known to have or that demonstrates advantageous properties when administered alone or with a compound of any of the formulae herein. Drugs that could be usefully combined with these compounds include natural or synthetic corticosteroids, particularly prednisone and its derivatives, cyclooxygenase-2 inhibitors, nonsteroidalantiinflammatory agents (NSAIDs, e.g., aspirin, diclofenac, diflunisal, etodolac, fenoprofen, floctafenine, flurbiprofen, ibuprofen, indomethacin, ketoprofen, meclofenamate, mefenamic acid, meloxicam, nabumetone, naproxen, oxaprozin, phenylbutazone, piroxicam, sulindac, tenoxicam, tiaprofenic acid, tolmetin), disease-modifying antirheumatic drugs (DMARDS, e.g., adalimumab, azathioprine, chloroquine, hydroxychloroquine, cyclosporin (Cyclosporine A), D-penicillarnine, etanercept, gold salts (sodium aurothiomalate, auranofin), infliximab, leflunomide, methotrexate (MTX), minocycline, sulfasalazine (SSZ)), immunosuppressive agents, 5-lipoxygenase inhibitors, $LTB_4$ antagonists, $LTA_4$ hydrolase inhibitors, monoclonal antibodies targeting cells of the immune system, antibodies or soluble receptors or receptor fusion proteins targeting immune or non-immune cytokines, and small molecule inhibitors of cell division, protein synthesis, DNA synthesis, pyrimidine synthesis, or mRNA transcription or translation, or inhibitors of immune cell differentiation or activation.

Such agents are described in detail in the art. Preferably, the second therapeutic agent is an agent useful in the treatment or prevention of a disease or condition selected from inflammatory disease (e.g., rheumatoid arthritis, rheumatoid spondylitis, osteoarthritis, gouty arthritis and other arthritic conditions); lymphoma; systemic lupus erthrematosis (SLE); blood vessel proliferative disorders; fibrotic disorders; mesangial cell proliferative disorders; metabolic disorders; sepsis, septic shock, endotoxic shock, Gram-negative sepsis, toxic shock syndrome, asthma, adult respiratory distress syndrome, stroke, reperfusion injury, CNS injuries such as neural trauma and ischemia, psoriasis, restenosis, cerebral malaria, chronic pulmonary inflammatory disease, silicosis, pulmonary sarcosis, bone resorption diseases such as osteoporosis, graft-versus-host reaction, Crohn's Disease, ulcerative colitis including inflammatory bowel disease (IBD) and pyresis); allergies; asthma; thrombosis; nervous system diseases; and cancer (e.g., breast, stomach, ovary, colon, lung, brain, larynx, lymphatic system, genitourinary tract, ovarian, gastric, bone, and pancreatic cancer).

Even more preferably the second therapeutic agent coformulated with a compound of this invention is an agent useful in the treatment of p38-mediated disease/disorders.

In another embodiment, the invention provides separate dosage forms of a compound of this invention and a second therapeutic agent that are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the invention, the compound of the present invention is present in an effective amount. As used herein, the term "effective amount" refers to an amount which, when administered in a proper dosing regimen, is sufficient to reduce or ameliorate the severity, duration or progression of the disorder being treated, prevent the advancement of the disorder being treated, cause the regression of the disorder being treated, or enhance or improve the prophylactic or therapeutic effect(s) of another therapy.

The interrelationship of dosages for animals and humans (based on milligrams per meter squared of body surface) is described in Freireich et al., (1966) Cancer Chemother Rep 50: 219. Body surface area may be approximately determined from height and weight of the patient. See, e.g., Scientific Tables, Geigy Pharmaceuticals, Ardley, N.Y., 1970, 537. An effective amount of a compound of this invention can range from about 0.001 mg/kg to about 500 mg/kg, more preferably 0.01 mg/kg to about 50 mg/kg, more preferably 0.1 mg/kg to about 2.5 mg/kg. Effective doses will also vary, as recognized by those skilled in the art, depending on the diseases treated, the severity of the disease, the route of administration, the sex, age and general health condition of the patient, excipient usage, the possibility of co-usage with other therapeutic treatments such as use of other agents and the judgment of the treating physician.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

It is expected that some of the second therapeutic agents referenced above will act synergistically with the compounds of this invention. When this occurs, its will allow the effective dosage of the second therapeutic agent and/or the compound of this invention to be reduced from that required in a monotherapy. This has the advantage of minimizing toxic side effects of either the second therapeutic agent of a compound of this invention, synergistic improvements in efficacy, improved ease of administration or use and/or reduced overall expense of compound preparation or formulation.

Methods of Treatment

According to another embodiment, the invention provides a method of treating a subject suffering from or susceptible to a disease or disorder or symptom thereof (e.g., those delineated herein) comprising the step of administering to said subject an effective amount of a compound or a composition of this invention. Such diseases are well known in the art and are also disclosed herein.

In one aspect, the method of treating involves treatment of a disorder that is mediated by the protein kinase, e.g., p38.

More specifically, the invention provides methods for treating or preventing inflammation; arthritis, rheumatoid arthritis, spondylarthropathies, gouty arthritis, osteoarthritis, systemic lupus erthematosus, juvenile arthritis, and other arthritic conditions; neuroinflammation; allergy, Th2 mediated diseases; pain, neuropathic pain; fever; pulmonary disorders, lung inflammation, adult respiratory distress syndrome, pulmonary sarcoisosis, asthma, silicosis, chronic pulmonary inflammatory disease, and chronic obstructive pulmonary disease (COPD); cardiovascular disease, arteriosclerosis, myocardial infarction (including post-myocardial infarction indications), thrombosis, congestive heart failure, cardiac reperfusion injury, as well as complications associated with hypertension and/or heart failure such as vascular organ damage, restenosis; cardiomyopathy; stroke including ischemic and hemorrhagic stroke; reperfusion injury; renal reperfusion injury; ischemia including stroke and brain ischemia, and ischemia resulting from cardiac/coronary bypass; neurotkauma and brain trauma including closed head injury; brain edema; neurodegenerative disorders; liver disease and nephritis; gastrointestinal conditions, inflammatory bowel disease, Crohn's disease, gastritis, irritable bowel syndrome, ulcerative colitis; ulcerative diseases, gastric ulcers; ophthalmic diseases, retinitis, retinopathies, uveitis, ocular photophobia, acute injury to the eye tissue and ocular traumas such as posttraumatic glaucoma, traumatic optic neuropathy, and central retinal artery occlusion (CRAO); periodontal disease; ophthalmological conditions, retinitis, retinopathies (including diabetic retinopathy), uveitis, ocular photophobia, nonglaucomatous optic nerve atrophy, and age related macular degeneration (ARMD) (including ARMD-atrophic form), corneal graft rejection, ocular neovascularization, retinal neovascularization, neovascularization following injury or infection, retrolental fibroplasias, neovascular glaucoma; glaucoma including primary open angle glaucoma (POAG), juvenile onset primary open-angle glaucoma, angle-closure glaucoma, pseudoexfoliative glaucoma, anterior ischemic optic neuropathy (AION), ocular hypertension, Reiger's syndrome, normal tension glaucoma, neovascular glaucoma, ocular inflammation and corticosteroid-induced glaucoma; diabetes; diabetic nephropathy; skin-related conditions, psoriasis, eczema, burns, dermatitis, keloid formation, scar tissue formation, angiogenic disorders; viral and bacterial infections, sepsis, septic shock, gram negative sepsis, malaria, meningitis, HIV infection, opportunistic infections, cachexia secondary to infection or malignancy, cachexia secondary to acquired immune deficiency syndrome (AIDS), AIDS, ARC (AIDS related complex), pneumonia, herpes virus; myalgias due to infection; influenza; endotoxic shock; toxic shock syndrome; autoimmune disease, graft vs. host reaction and allograft rejections; treatment of bone resorption diseases, osteoporosis; multiple sclerosis; disorders of the female reproductive system, endometriosis; hemaginomas, infantile hemagionmas, angiofibroma of the nasopharynx, avascular necrosis of bone; benign and malignant tumors/neoplasia, cancer, colorectal cancer, brain cancer, bone cancer, epithelial call-derived neoplasia (epithelial carcinoma), basal cell carcinoma, adenocarcinoma, gastrointestinal cancer, lip cancer, mouth cancer, esophageal cancer, small bowel cancer, stomach cancer, colon cancer, liver cancer, bladder cancer, pancreas cancer, ovarian cancer, cervical cancer, lung cancer, breast cancer, skin cancer, squamus cell and/or basal cell cancers, prostate cancer, renal cell carcinoma, and other known cancers that affect epithelial cells throughout the body; leukemia; lymphoma; systemic lupus erthrematosis (SLE); angiogenesis including neoplasia; metastasis; central nervous system disorders, central nervous system disorders having an inflammatory or apoptotic component, Alzheimer's disease, Parkinson's disease, Huntington's disease, amyotrophic lateral sclerosis, spinal cord injury, and peripheral neuropathy; Canine B-Cell Lymphoma. Compounds of the invention are also useful for preventing the production or expression of cyclooxygenase-2, or cyclooxygenase-2 activity.

In another embodiment, the invention provides a method of modulating the activity of a protein kinase, (e.g. protein tyrosine kinase, kinases listed herein) in a cell comprising contacting a cell with one or more compounds of any of the formulae herein.

In another embodiment, the above method of treatment comprises the further step of co-administering to said patient one or more second therapeutic agents. The choice of second therapeutic agent may be made from any second therapeutic agent known to be useful for indications herein.

The term "co-administered" as used herein means that the second therapeutic agent may be administered together with a compound of this invention as part of a single dosage form (such as a composition of this invention comprising a compound of the invention and an second therapeutic agent as described above) or as separate, multiple dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administration of a composition of this invention comprising both a compound of the invention and a second therapeutic agent to a subject does not preclude the separate administration of that same therapeutic agent, any other second therapeutic agent or any compound of this invention to said subject at another time during a course of treatment.

Effective amounts of these second therapeutic agents are well known to those skilled in the art and guidance for dosing may be found in patents and published patent applications referenced herein, as well as in Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In one embodiment of the invention where a second therapeutic agent is administered to a subject, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

In yet another aspect, the invention provides the use of a compound of any of the formulae herein (e.g., Formula I) alone or together with one or more of the above-described second therapeutic agents in the manufacture of a medicament, either as a single composition or as separate dosage forms, for treatment or prevention in a subject of a disease, disorder or symptom set forth above. Another aspect of the invention is a compound of the formulae herein for use in the treatment or prevention in a subject of a disease, disorder or symptom thereof delineated herein.

In other aspects, the methods herein include those further comprising monitoring subject response to the treatment administrations. Such monitoring may include periodic sampling of subject tissue, fluids, specimens, cells, proteins, chemical markers, genetic materials, etc. as markers or indicators of the treatment regimen. In other methods, the subject is prescreened or identified as in need of such treatment by assessment for a relevant marker or indicator of suitability for such treatment.

In one embodiment, the invention provides a method of monitoring treatment progress. The method includes the step of determining a level of diagnostic marker (Marker) (e.g., any target or cell type delineated herein modulated by a compound herein) or diagnostic measurement (e.g., screen, assay) in a subject suffering from or susceptible to a disorder or symptoms thereof delineated herein, in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

In certain method embodiments, a level of Marker or Marker activity in a subject is determined at least once. Comparison of Marker levels, e.g., to another measurement of Marker level obtained previously or subsequently from the same patient, another patient, or a normal subject, may be useful in determining whether therapy according to the invention is having the desired effect, and thereby permitting adjustment of dosage levels as appropriate. Determination of Marker levels may be performed using any suitable sampling/expression assay method known in the art or described herein. Preferably, a tissue or fluid sample is first removed from a subject. Examples of suitable samples include blood, urine, tissue, mouth or cheek cells, and hair samples containing roots. Other suitable samples would be known to the person skilled in the art. Determination of protein levels and/or mRNA levels (e.g., Marker levels) in the sample can be performed using any suitable technique known in the art, including, but not limited to, enzyme immunoassay, ELISA, radio-labelling/assay techniques, blotting/chemiluminescence methods, real-time PCR, and the like.

The present invention also provides kits for use to treat diseases, disorders, or symptoms thereof, including those delineated herein. These kits comprise: a) a pharmaceutical composition comprising a compound of any of the formula herein (e.g., Formula I) or a salt thereof; or a prodrug, or a salt of a prodrug thereof; or a hydrate, solvate, or polymorph thereof, wherein said pharmaceutical composition is in a container; and b) instructions describing a method of using the pharmaceutical composition to treat the disease, disorder, or symptoms thereof, including those delineated herein.

The container may be any vessel or other sealed or sealable apparatus that can hold said pharmaceutical composition. Examples include bottles, divided or multi-chambered holders bottles, wherein each division or chamber comprises a single dose of said composition, a divided foil packet wherein each division comprises a single dose of said composition, or a dispenser that dispenses single doses of said composition. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle, which is in turn contained within a box. Preferably, the container is a blister pack.

The kit may additionally comprising information and/or instructions for the physician, pharmacist or subject. Such memory aids include numbers printed on each chamber or division containing a dosage that corresponds with the days of the regimen which the tablets or capsules so specified should be ingested, or days of the week printed on each chamber or division, or a card which contains the same type of information.

All references cited herein, whether in print, electronic, computer readable storage media or other form, are expressly incorporated by reference in their entirety, including but not limited to, abstracts, articles, journals, publications, texts, treatises, technical data sheets, internet web sites, databases, patents, patent applications, and patent publications.

EXAMPLES

Preparation of Advanced Intermediate: 3-(4-Hydroxy-2-methylsulfanyl-6-oxo-6H-pyrimidin-1-yl)-4-methyl-benzoic Acid Methyl Ester (A)

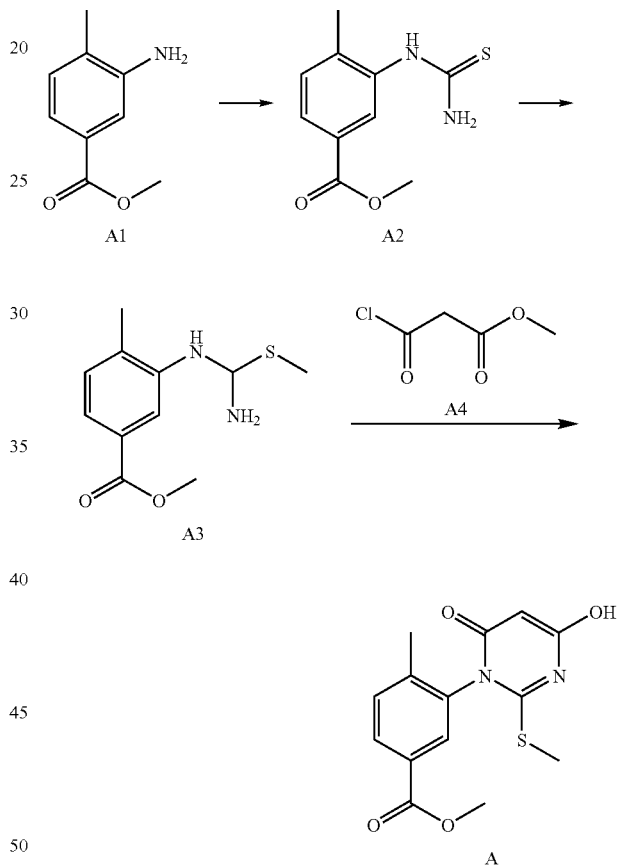

Step 1: Benzyl chloride (21.8 g, 0.155 mol) was added drop-wise to a well-stirred solution of ammonium thiocyanate (13.0 g, 0.171 mol) in acetone (200 mL). The mixture was refluxed for 15 min, compound A1 (25.6 g, 0.455 mol) was added slowly portion-wise. After 1 h, the reaction mixture was poured into water (500 mL) and the bright yellow solid was isolated by filtration. The crude solid was stirred at room temperature with an excess anhydrous potassium carbonate in methanol (700 mL) for 2 h. Then the solvent was removed under reduced pressure and the crude product was extracted with ethyl acetate and washed with water. The organic layer was dried over anhydrous $Na_2SO_4$ and concentrated to give a white solid. The solid was stirred in ether for 15 min and filtered to give compound A2 (11.5 g, 33% yield) as white solid.

Step 2: To a suspension of compound A2 (28.3 g, 0.126 mol) in methanol (280 mL) at 0° C., was added iodomethane (20.6 g, 0.145 mol) and stirred at room temperature for 30 min. The reaction mixture was then heated to reflux for 15 min to a clear solution. It was concentrated under reduced pressure and the residue was dried in vacuo, dissolved in dichloromethane (DCM) (500 mL). The solution was cooled to −5° C., added NMM (25.56 g, 0.253 mol), followed by the drop-wise addition of a solution of compound A4 (25.87 g, 0.19 mol) in DCM (60 mL). The resulting mixture was stirred at room temperature overnight under N₂ atmosphere. The mixture was cooled to −5° C. and added an additional amount of NMM (8.9 g, 0.088 mol) and A4 (12.07 g, 0.088 mol). The mixture was stirred at room temperature for 2h, cooled to 10° C., added water (400 mL). The mixture was stirred for 30 min. The interfacial solid was filtered, washed with Water and dried to give compound A (27.9 g, 72.0% yield).

Preparation of Advanced Intermediate: 3-{4-[(2,4-difluorophenyl)methoxyl]-5-chloro-2-methylthio-6-oxohydropyrimidinyl}-4-methylbenzoic acid (B)

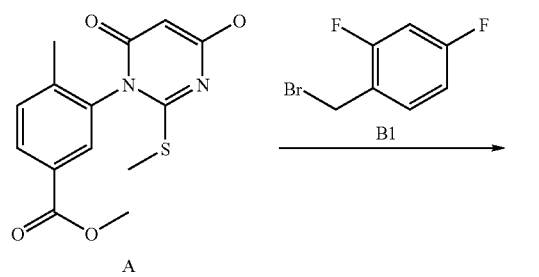

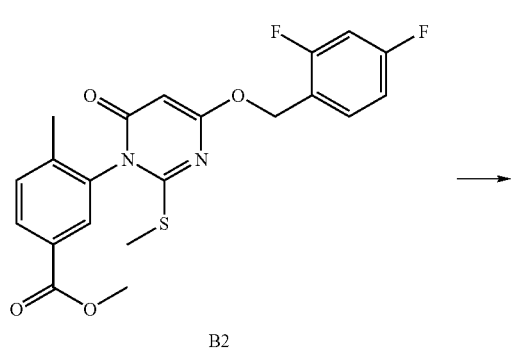

B2

Step 1: To a solution of A (1.0 g, 3.3mmol) in DMF (5 mL) was added K2CO3 (0.677 g, 4.9 mmol), followed by the addition of B1 (0.744 g, 3.6 mmol) and stirred at 0° C. for 15 min. After stirring at room temperature for 30 min, DMF was evaporated in vacuo and the residue was portioned between EA (20 mL) and water (15 mL). The organic phase was washed with water, dried with Na2SO4 and concentrated. The resulting material was purified by column chromatography to afford B2 (1.06 g, 75% yield) as white solid.

Step 2: A mixture of B2 (1.06 g, 2.45 mmol) in 2N aq. NaOH (4.9 mL, 9.81 mmol) and dioxane (2.7 mL) was stirred at room temperature for 1.5 h. The resulting clear solution was diluted with water, acidified with 5% citric acid and extracted with EA. The combined organic extracts were washed with water, dried and concentrated to afford B3 (1.01 g, 98% yield).

Step 3: A mixture of B3 (1.01 g, 2.45 mmol) and NCS (0.36 g, 2.7 mmol) in dichloroethane (20 mL) containing dichloroacetic acid (0.791 g, 6.13 mmol) was heated at 65° C. for 3 h under N2 atmosphere. The mixture was concentrated under reduced pressure and the residue was partioned between EA and water. The organic phase was washed with water, dried and concentrated under reduced pressure to provide B (0.986 g, 89% yield).

Preparation of Advanced Intermediate: 3-[5-Chloro-4-(2,4-difluoro-benzyloxy)-6-oxo-6H-pyrimidin-1-yl-]4-methyl-benzoic acid (C)

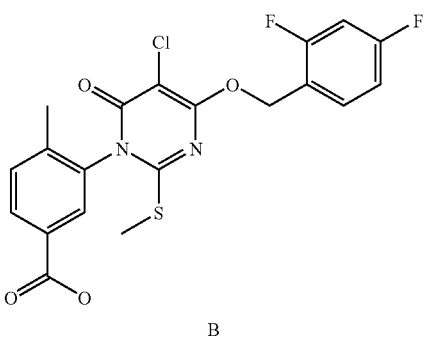

B

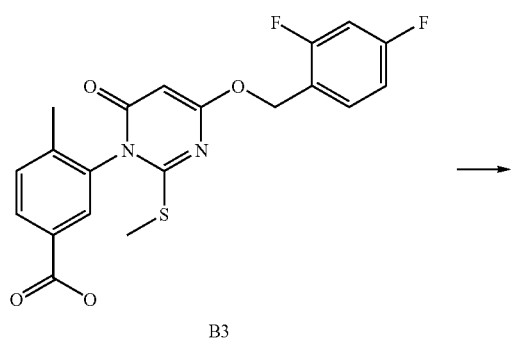

B3

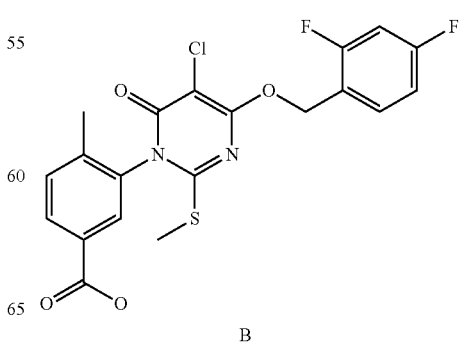

B

29
-continued

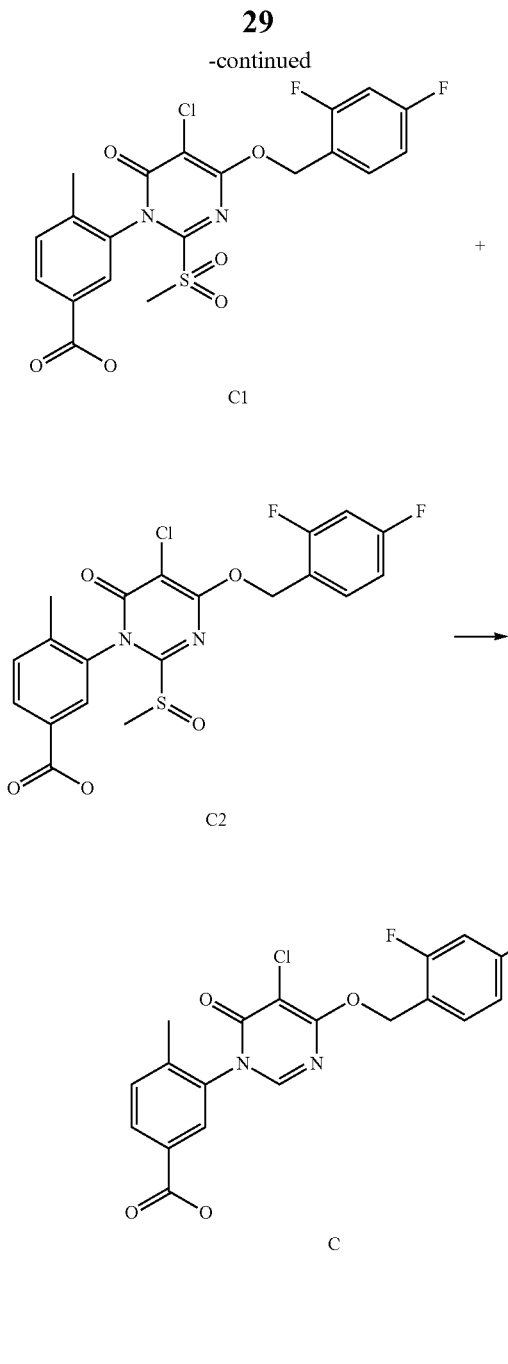

Step 1: To a solution of B (15.45 g, 34.1 mmol) in 98% formic acid (90 mL) was added 30% H2O2 solution (15 mL) drop-wise at r.t. The resulting mixture was stirred at room temperature overnight and evaporated. The residue was triturated with methanol for three times to provide a mixture of C1 and C2. (16.03 g, about 99%).

Step 2: NaBH4 (2.59 g, 68.3 mmol) was slowly added to a solution of C1 and C2 (16.03 g, about 34 mmol) in MeOH (130 mL) at r.t. The resulting mixture was stirred at r.t. for 4 h. After the reaction was complete, MeOH was evaporated and 80 mL of water was added. The mixture was acidified with 3N HCl until pH=4 and extracted with EA for several times. The combined EA phase was dried, concentrated and re-crystallized from EA to provide C (6.03 g, about 40%) as white solid.

30

Example 1

Preparation of 3-[5-Chloro-4-(2,4-difluoro-benzyloxy)-6-oxo-6H-pyrimidin-1-yl]-N-[(R)-2-(2-methoxy-ethyl)-3-oxo-isoxazolidin-4-yl]-4-methyl-benzamide

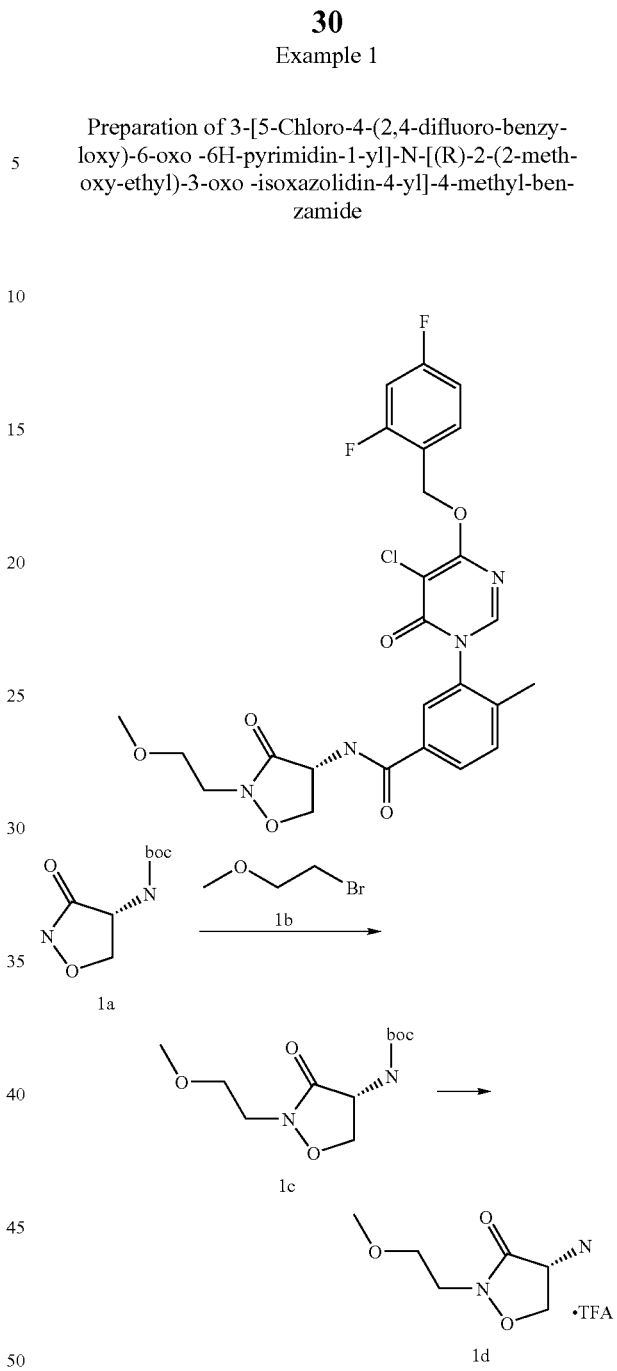

Step 1: Compound 1a (202 mg, 1.0 mmol), 1b (167 mg, 1.2 mmol), KI (174 mg, 1.05 mmol), K2CO3 (690 mg, 5.0 mmol) and acetonitrile (20 mL) were mixed in a microwave vial. The resulting mixture was reacted under microwave condition at 140° C. for 1 h. After being cooled, the mixture was filtered. The filtrate was evaporated and the residue was purified by column chromatography (EA: PE=1:3) to provide 1c (131 mg, 50.4%).

Step 2: To a solution of 1c (96 mg, 0.37 mmol) in DCM (3 mL) was added TFA (1 mL) drop-wise at room temperature. The mixture was stirred for 4 h and evaporated to provide crude 1d which was used for the next step directly.

Step 3: The solution of C (100 mg, 0.246 mmol), HATU (140 mg, 0.37 mmol) and DIEA (159 mg, 1.23mmol) in DMF (10 mL) was stirred at r.t. for 0.5 h. Compound 1d from last step in 2 mL of DMF was added drop-wise. The resulting mixture was stirred at r.t. overnight. LC-MS and TLC were used to detect completion of the reaction. DMF was evaporated in vacuo. The residue was purified by column chromatography (PE:EA=1:2), then Prep TLC (PE:EA=1:2) to provide the title compound (107 mg, 79% yield). 1H NMR (CD3OD, 300 MHz): δ=8.32-8.33(d, 1H), 7.92-7.96(m, 1H), 7.80(s, 1H), 7.53-7.65(m, 2H), 6.99-7.06(m, 2H), 5.48-5.65 (q, 2H), 5.13-5.20(m, 1H), 4.62-4.68 (t, 1H), 4.13-4.20(m, 1H), 3.75-3.80(m, 2H), 3.56-3.64(m, 2H), 3.46(s, 3H), 2.20 (s, 3H). LC-MS: 549.1 (M+1)$^+$.

Example 2

Preparation of 3-[5-Chloro-4-(2,4-difluoro-benzyloxy)-6-oxo-6H-pyrimidin-1-yl]-N-[(R)-2-(2-hydroxy-ethyl)-3-oxo-isoxazolidin-4-yl]-4-methyl-benzamide

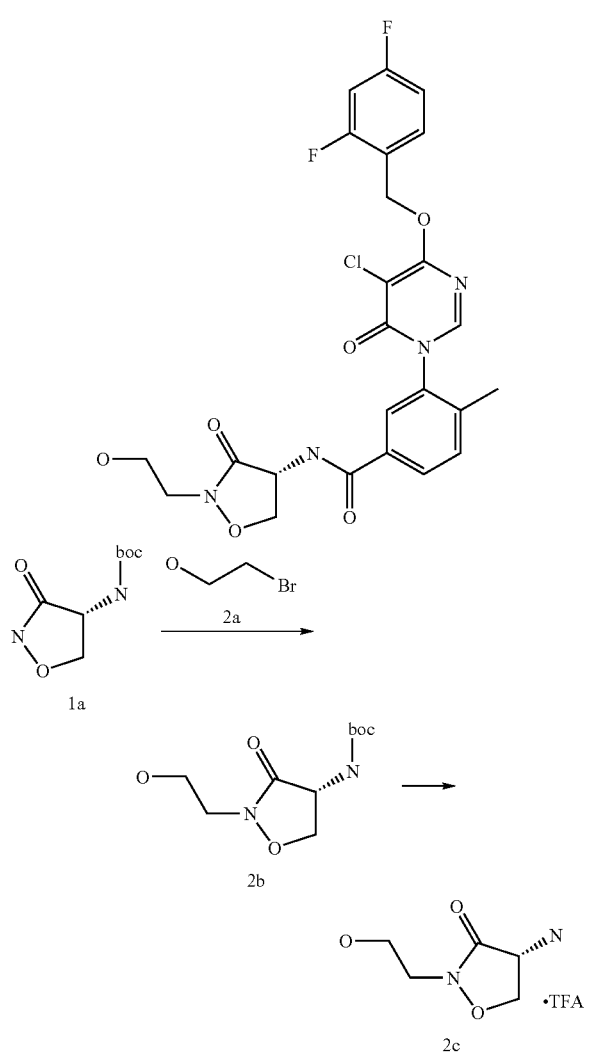

Step 1: The mixture of 1a (200 mg, 0.99 mmol), 2a (136 mg, 1.09 mmol), KI (173 mg, 1.04 mmol) and K2CO3 (273 mg, 1.99 mmol) in DMF (5 mL) was stirred at r.t. for 2 days, then heated to 60° C. for 3 h. After being cooled, the mixture was evaporated and the residue was purified by column chromatography (EA: MeOH=30:1) to provide 2b (60 mg, 24.7%).

Step 2: The following de-Boc and final coupling steps were similar to that of Example 1 to provide title compound (36 mg, 45.6% yield) as white solid. 1H NMR (CD3OD, 300 MHz): δ=8.31(d, 1H), 7.90-7.93(m, 1H), 7.79-7.80(m, 1H), 7.49-7.62(m, 2H), 6.97-7.04(m, 2H), 5.58-5.59(q, 2H), 5.13-5.16(m, 1H), 4.61-4.67 (t, 1H), 4.14-4.22(m, 1H), 3.67-3.75 (m, 4H), 2.19(s, 3H). LC-MS: 533.0 (M−1)$^+$. ; :

Example 3

Preparation of 3-[5-Chloro-4-(2,4-difluoro-benzyloxy)-6-oxo-6H-pyrimidin-1-yl]-4-methyl-N-((R)-2-methyl-3-oxo-isoxazolidin-4-yl)-benzamide

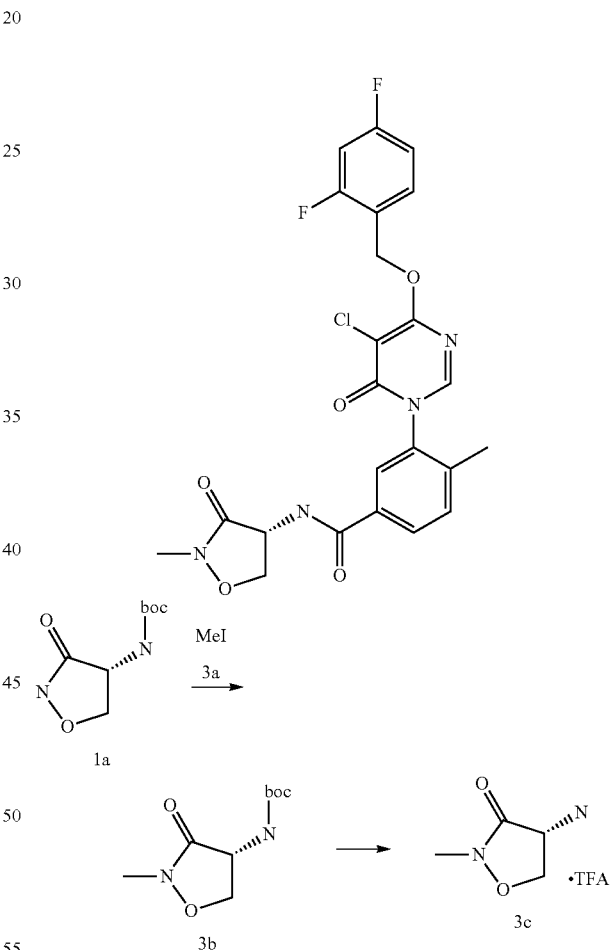

Step 1: The mixture of 1a (200 mg, 0.99 mmol), MeI (155 mg, 1.09 mmol) and K2CO3 (205 mg, 1.49 mmol) in DMF (5 mL) was stirred at r.t. for for 3 h. After the reaction was complete, the mixture was evaporated and the residue was purified by column chromatography (EA: PE=1:5) to provide 3b (164 mg, 76.6%).

Step 2: The following de-Boc and final coupling steps were similar to that of Example 1 to provide title compound (87 mg, 70% yield) as white solid. 1H NMR (CD3OD, 300 MHz): δ=8.31(s, 1H), 7.78-7.94(m, 2H), 7.52-7.65(m, 2H), 7.98-7.06(m, 2H), 5.59-5.60(q, 2H), 5.08-5.11(t, 1H), 4.59-4.65 (t, 1H), 4.13-4.21(m, 1H), 3.19(s, 3H), 2.20(s, 3H). LC-MS: 505.1 (M+1)⁺.

Example 4

Preparation of 3-[5-Chloro-4-(2,4-difluoro-benzyloxy)-6-oxo-1H-pyrimidin-1-yl]-4-methyl-N-[(R)-3-oxo-2-(tetrahydro-pyran-4-yl)-isoxazolidin-4-yl]-benzamide

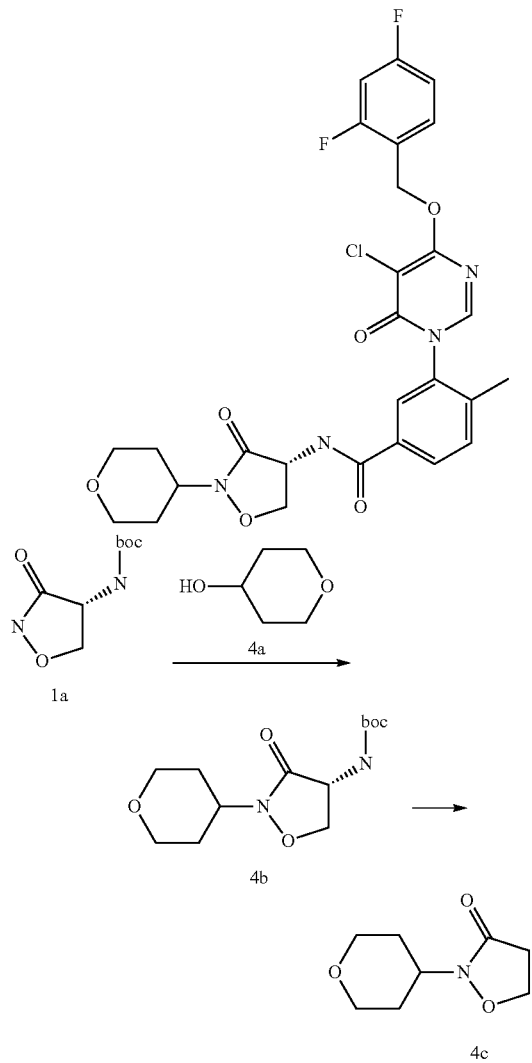

Step 1: To a solution of 1a (800 mg, 3.96 mmol), 4a (606 mg, 5.94 mmol) and PPh3 (3.1 g, 11.9 mmol) in THF (30 mL), was added DEAD (2.1 g, 11.9 mmol) in THF (10 mL) dropwise at −60° C. After the addition was complete, the reaction mixture was warmed to r.t. gradually and stirred for 3 days. The mixture was then evaporated and the residue was purified by column chromatography (EA:PE=4:1) to provide 4b (365 mg, 32%) as a clear oil which still contained small amount of POPh3.

Step 2: The following de-Boc and coupling steps were similar to that of Example 1 to provide title compound (97 mg, 69% yield) as white solid. 1H NMR (CD3OD, 300 MHz): δ=8.31(s, 1H), 7.91-7.95(dd, 1H), 7.79-7.80(t, 1H), 7.52-7.65(m, 2H), 6.99-7.05(m, 2H), 5.55-5.64(q, 2H), 5.10-5.17(m, 1H), 4.62-4.67 (t, 1H), 4.12-4.24(m, 2H), 3.97-4.01 (m, 2H), 3.45-3.52(m, 2H), 2.20(s, 3H), 1.93-2.06(m, 2H), 1.68-1.80(m, 2H). LC-MS: 575.1 (M+1)⁺.

Example 5

Preparation of 3-[5-Chloro-4-(2,4-difluoro-benzyloxy)-6-oxo-6H-pyrimidin-1-yl]-N[(S)-1-(2-methoxy-ethyl)-2-oxo-pyrrolidin-3-yl]-4-methyl-benzamide

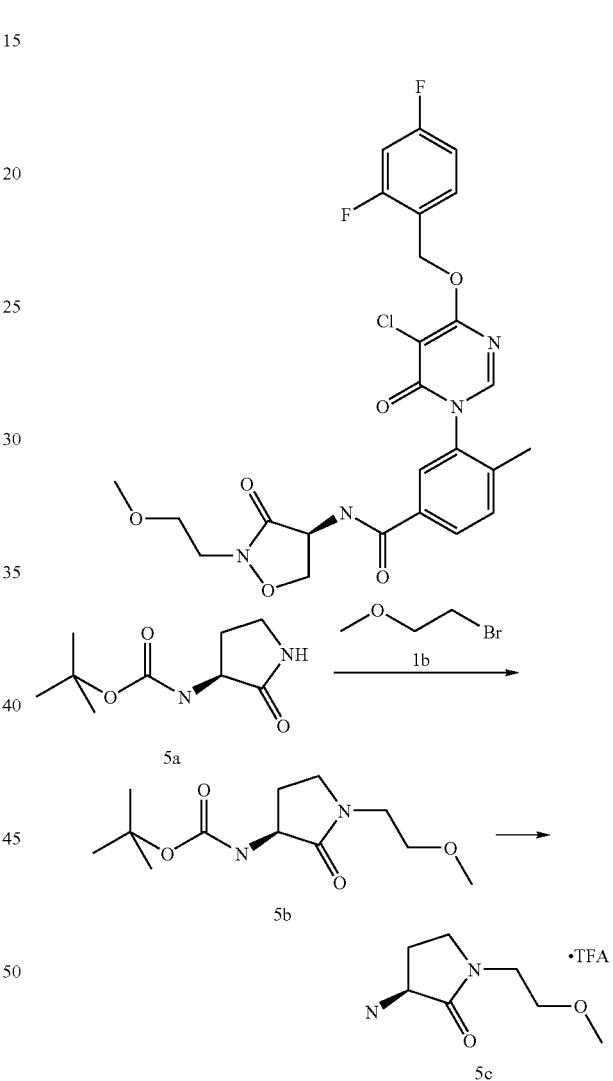

Step1: To a solution of 5a (100 mg, 0.5 mmol) in DMF (5 mL) was added 60% NaH (21 mg, 0.53 mmol) at 0° C. After stirring for 1 h, the mixture was added compound 1b (67.5 mg, 0.49 mmol). The obtained mixture was stirred overnight at r.t. and evaporated. The residue was purified by column chromatography (EA:PE=1:1) to provide 5b (68 mg, 54%).

Step 2: The following de-Boc and final coupling steps were similar to that of Example 1 to provide title compound (103 mg, 76.3% yield) as white solid. 1H NMR (CD3OD, 300 MHz): δ=8.32-8.33(d, 1H), 7.92-7.96(m, 1H), 7.78-7.79(d, 1H), 7.52-7.66(m, 2H), 6.99-7.06(m, 2H), 5.55-5.65(q, 2H), 4.68-4.77(m, 1H), 3.43-3.58(m, 6H), 3.34(s, 3H), 2.47-2.51 (m, 1H), 2.20(s, 3H), 2.00-2.10(m, 1H). LC-MS: 547.1 (M+1)+.

Example 6

Preparation of 3-[5-Chloro-4(2,4-difluoro-benzyloxy)-6-oxo-6H-pyrimidin-1-yl]-N—[(S)-1-(2-methoxy-ethyl)-2,5-dioxo-pyrrolidin-3-yl]-4-methyl-benzamide

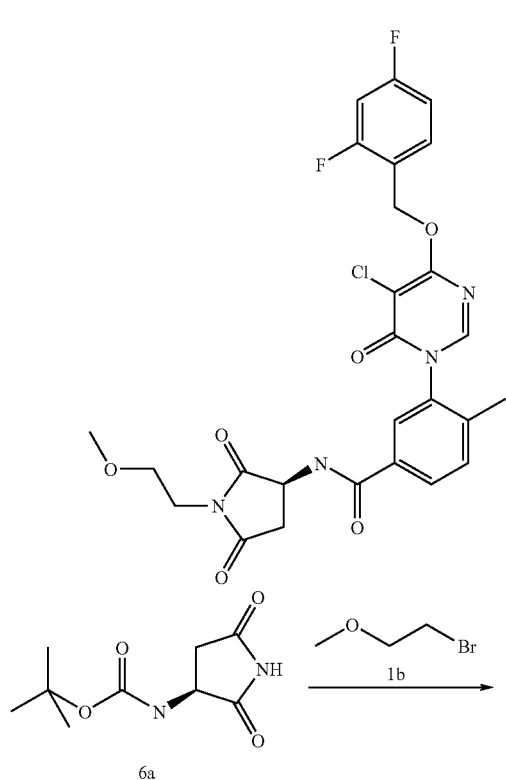

3.57(t, 2H), 3.32(s, 3H), 3.05-3.14(q, 1H), 2.72-2.81(dd, 1H), 2.19(s, 3H). LC-MS: 561.1 (M+1)+.

Example 7

Preparation of 3-[5-Chloro-4-(2,4-difluoro-benzyloxy)-6-oxo-6H-pyrimidin-1-yl]-N-[(S)-1-(2-hydroxy-ethyl)-2,5-dioxo-pyrrolidin-3-yl]-4-methyl-benzamide

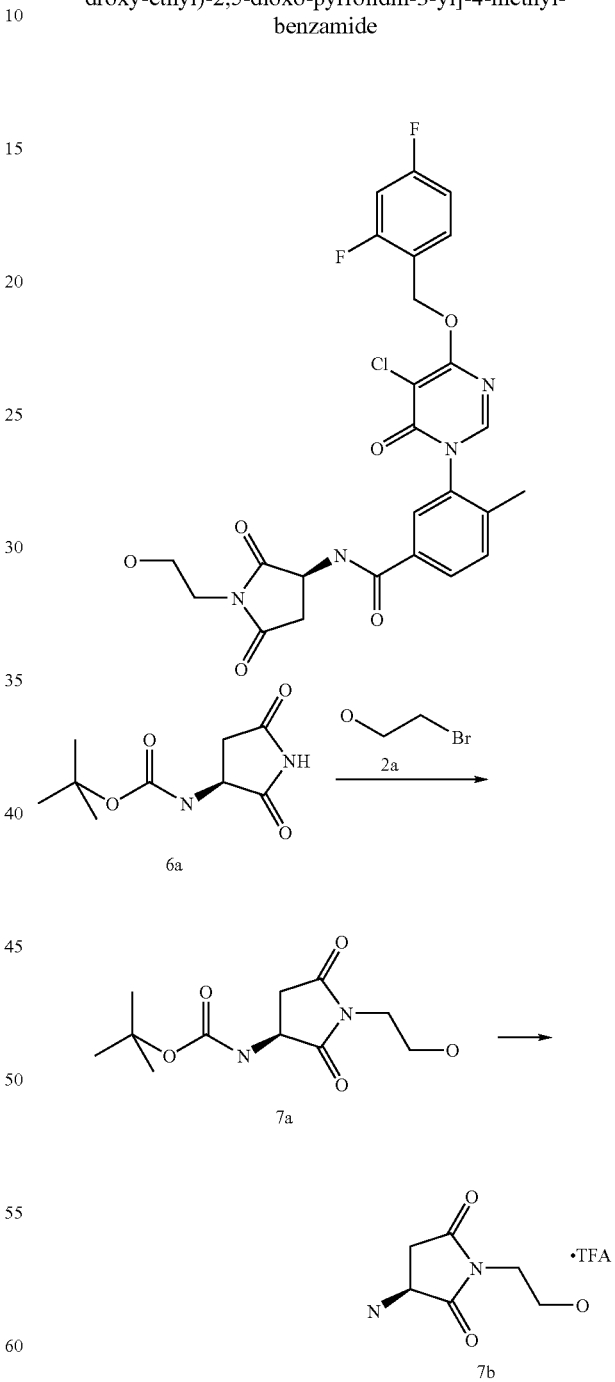

The synthesis was similar to that of Example 1 to provide title compound (115 mg, 83.3% yield) as white solid. 1H NMR (CD3OD, 300 MHz): δ=8.30-8.31(m, 1H), 7.88-7.91 (d, 1H), 7.76(s, 1H), 7.52-7.65(m, 2H), 6.98-7.05(m, 2H), 5.58-5.59(q, 2H), 4.63-4.68(m, 1H), 3.70-3.74(q, 2H), 3.54-

The synthesis was similar to that of Example 2 to provide title compound (61 mg, 77.4% yield) as white solid. 1H NMR (CD3OD, 300 MHz): δ=8.31-8.32(d, 1H), 7.90-7.93(m, 1H), 7.77(s, 1H), 7.54-7.65(m, 2H), 6.99-7.05(m, 2H), 5.55-5.64

(q, 2H), 4.64-4.69(q, 1H), 3.69-3.70(t, 4H), 3.07-3.16(q, 1H), 2.74-2.81(dd, 1H), 2.21(s, 3H). LC-MS: 547.1 (M+1)$^+$.

Example 8

Preparation of 3-[5-Chloro-4-(2,4-difluoro-benzyloxy)-6-oxo-6H-pyrimidin-1-yl]-4-methyl-N-((S)-1-methyl-2,5-dioxo-pyrrolidin-3-yl)-benzamide

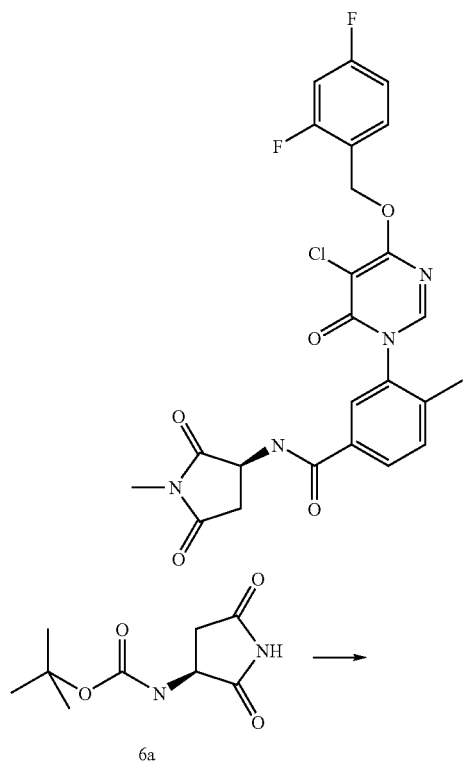

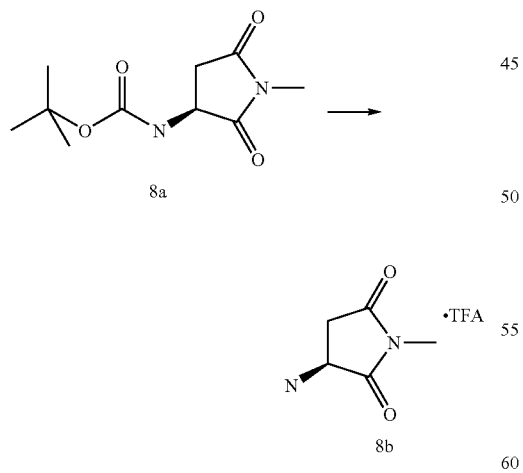

The synthesis was similar to that of Example 3 to provide title compound (92 mg, 80.7% yield) as white solid. 1H NMR (CD3OD, 300 MHz): δ=8.31-8.32(d, 1H), 7.88-7.92(m, 1H), 7.75-7.76(t, 1H), 7.53-7.65(m, 2H), 6.99-7.06(m, 2H), 5.55-5.64(q, 2H), 4.61-4.65(q, 1H), 3.04-3.13(q, 2H), 2.72-2.80 (dd, 1H), 2.18(s, 3H), LC-MS: 517.1 (M+1)$^+$.

p38α Biochemical Assay

The p38 α biochemical activity is measured by Upstate Ltd in Dundee, UK following this procedure: In a final reaction volume of 25 µl, p38α (h) (5-10 mU) is incubated with 25 mM Tris pH 7.5, 0.02 mM EGTA, 0.33 mg/ml myelin basic protein, 10 mM MgAcetate and [γ-$^{33}$P-ATP] (specific activity approx. 500 cpm/pmol concentration as required). The reaction is initiated by the addition of the MgATP mix. After incubation for 40 min. at room temperature, the reaction is stopped by the addition of 5 µl of a 3% phosphoric acid solution. 10 µl of the reaction is then spotted onto a P30 filtermat and washed three times for 5 min. in 75 mM phosphoric acid and once in methanol prior to drying and scintillation counting. Representative compounds demonstrate p38α inhibitory activity.

Cellular Assay: Inhibition of LPS Stimulated TNF-α Production in THP-1 Cells

THP-1 cells are maintained in RPMI 1640, containing 10% FBS at 37° C. and 5% CO$_2$.

THP-1 cells are plated at a density of 2×105 cells/ml and 150 µl/well (96 well plate) in RPMI-1640+3% FBS (3×105 cells/well). Compounds are serial diluted in DMSO and added to the THP-1 cells to a final concentration of 1% DMSO. Cells are incubated for 1hr at 37° C. Cytokine secretion is induced by stimulation with 100 ng/ml LPS for 4 hours at 37° C. Culture supernatant is harvested and Cytokine secretion into the supernatant was quantitated by ELISA.

R&D human TNF-α/TNFSF1A (Minneapolis, Minn., cat #DY210) ELISA used as per kit instructions with antibody dilutions as follows: 3 µg/ml capture antibody, 50 ng/ml detection antibody and 1:200 strepavidin-HRP dilution. Representative compounds demonstrate LPS inhibitory activity at <1 µM. In particular, the substituted heterocyclic compounds (Examples 2 and 3) are >10 times more potent in this assay than their corresponding non-substituted analog D shown below.

Example 2

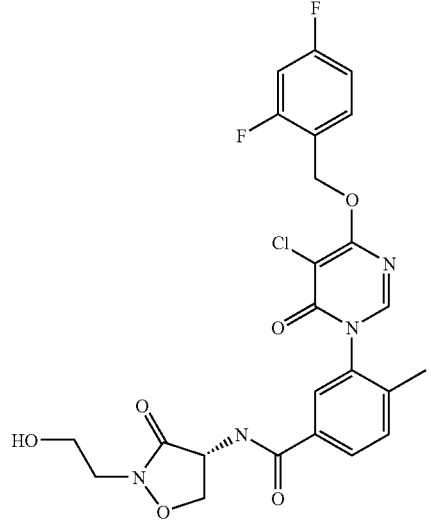

-continued

Example 3

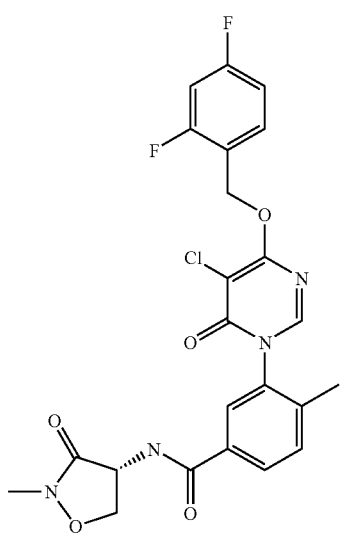

D

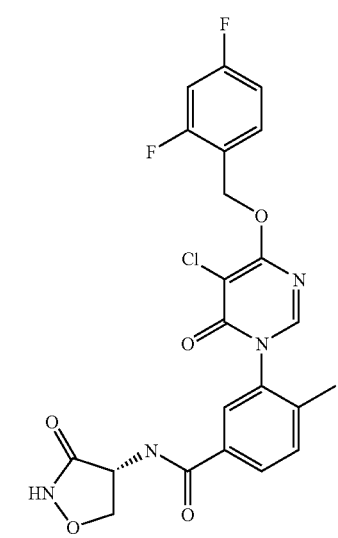

I claim:
1. A compound of formula I:

Formula I

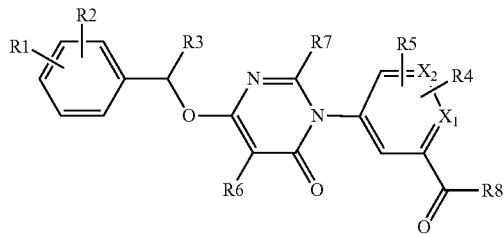

or a salt thereof; wherein:
R¹, R², R³, R⁴, R⁵, R⁶ are each independently hydrogen, halo, (C1-C3) alkyl, (C1-C3) alkoxy, and (C1-C3) alkylamino;
R⁷ is hydrogen, halo, (C1-C6) alkyl, (C1-C6) alkoxy, and (C1-C6) alkylamino wherein the alkyl is optionally substituted by one or two groups that are independently hydroxyl, (C1-C3) alkoxy, and (C1-C3) alkylamino;

R⁸ is C(O)NR⁹R¹⁰ or NHR¹¹;
R⁹ and R¹⁰ are each independently hydrogen, (C1-C6) alkyl, (C3-C8) cycloalkyl, (C3-C8) heterocyclyl, or R⁹ and R¹⁰ together with the nitrogen they are attached to form a (C3-C8) heterocycle;
R¹¹ is a (C3-C8) cycloalkyl substituted by 1, 2, 3, or 4 groups that are independently oxo, hydroxyl, (C1-C6) alkyl, (C1-C3) alkoxy, (C1-C3) alkylamino, heterocycle, amide, hydroxyl(C1-C6) alkyl, or (C1-C3)alkoxy (C1-C3)alkyl; or R¹¹ is a (C3-C8) heterocycle substituted by 2, 3, or 4 groups that are independently oxo, hydroxyl, (C1-C6) alkyl, (C1-C3) alkylamino, heterocycle, amide, hydroxyl(C1-C6)alkyl, or (C1-C3) alkoxy(C1-C3) alkyl;
X¹, X² are each independently N or CR⁴.

2. The compound of claim 1, wherein R¹¹ is a substituted (C3-C8) heterocycle exemplified by one of

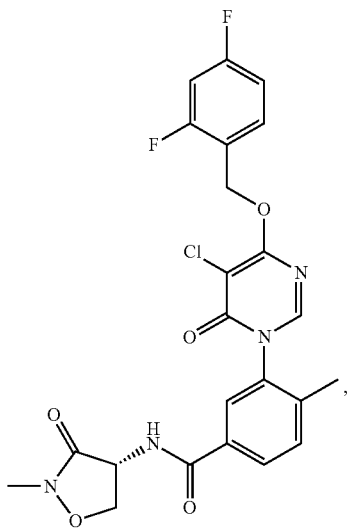

,

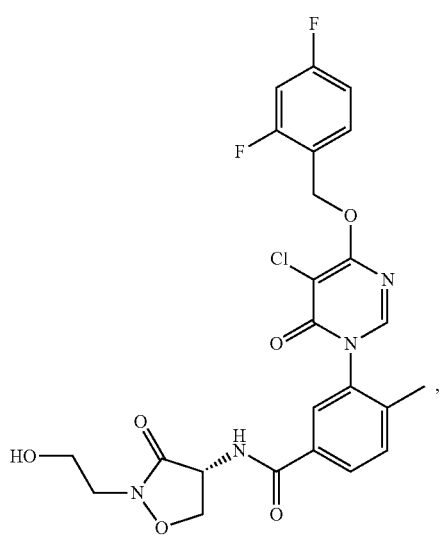

,

-continued
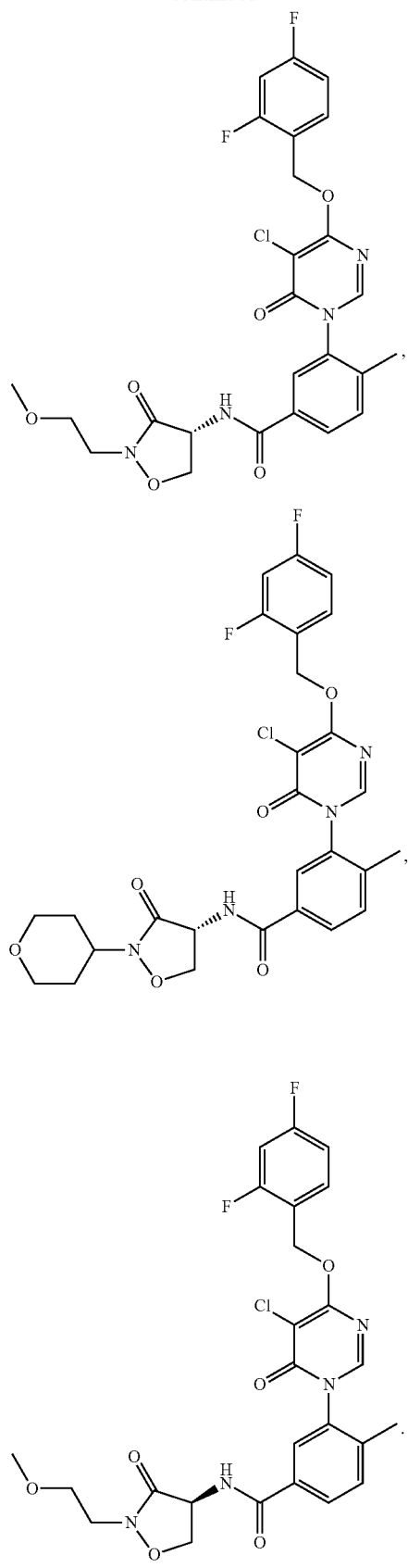
3. The compound of claim 1, wherein $R^{11}$ is a substituted (C3-C8) heterocycle exemplified by one of
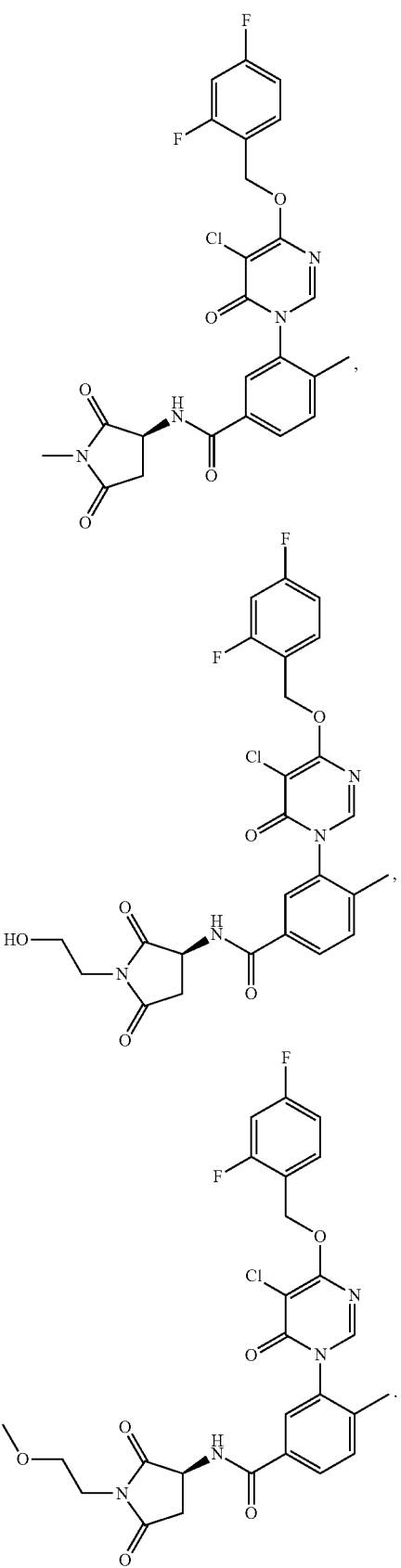

4. The compound of claim 1, wherein $R^{11}$ is a substituted (C3-C8) cycloalkyl exemplified by one of
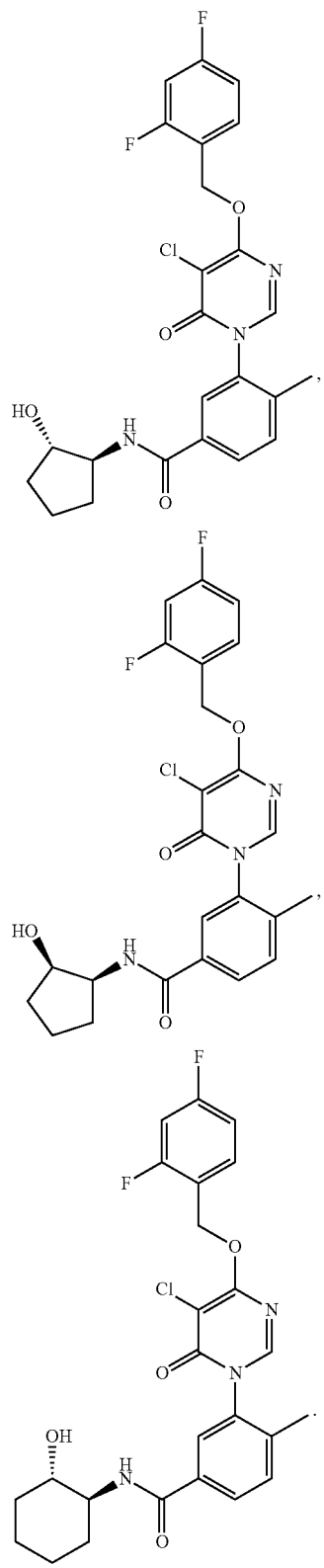
5. The compound of claim 1, wherein $R^8$ is C(O)NR$^9$R$^{10}$ exemplified by one of
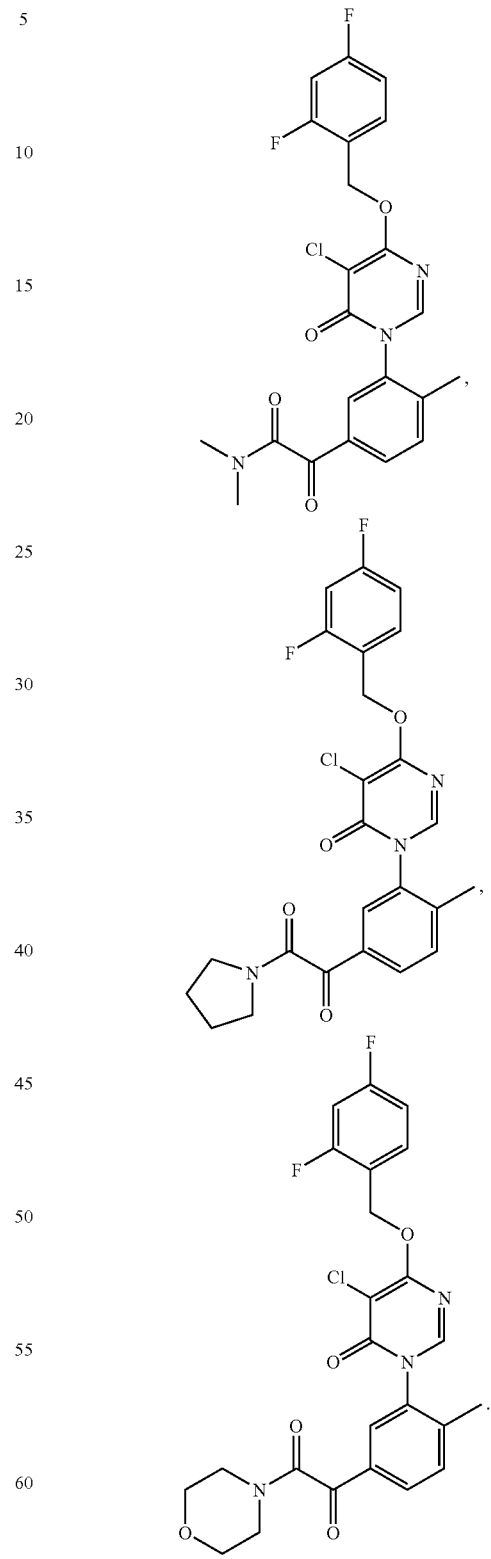
6. The compound of claim 1, wherein $X^1$ and $X^2$ are independently CR$^4$.
* * * * *